US009279137B2

(12) United States Patent
Sycheva et al.

(10) Patent No.: US 9,279,137 B2
(45) Date of Patent: Mar. 8, 2016

(54) MUTANT ACETOLACTATE SYNTHASE AND A METHOD FOR PRODUCING BRANCHED-CHAIN L-AMINO ACIDS

(71) Applicant: AJINOMOTO CO., INC., Tokyo (JP)

(72) Inventors: Elena Viktorovna Sycheva, Moscow region (RU); Vsevolod Aleksandrovich Serebryanyy, Moscow (RU); Tatyana Abramovna Yampolskaya, Moscow (RU); Ekaterina Sergeevna Preobrazhenskaya, Moscow (RU); Natalia Viktorovna Stoynova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/333,727

(22) Filed: Jul. 17, 2014

(65) Prior Publication Data

US 2014/0335574 A1 Nov. 13, 2014

Related U.S. Application Data

(63) Continuation of application No. 11/854,601, filed on Sep. 13, 2007, now abandoned.

(30) Foreign Application Priority Data

Sep. 13, 2006 (RU) .................... 2006132818

(51) Int. Cl.
*C12N 1/20* (2006.01)
*C12P 13/04* (2006.01)
*C12N 15/00* (2006.01)
*C12P 13/08* (2006.01)
*C12N 9/88* (2006.01)
*C12P 13/06* (2006.01)
*C12N 9/10* (2006.01)

(52) U.S. Cl.
CPC .............. *C12P 13/08* (2013.01); *C12N 9/1022* (2013.01); *C12N 9/88* (2013.01); *C12P 13/06* (2013.01); *C12Y 202/01006* (2013.01); *Y02P 20/52* (2015.11)

(58) Field of Classification Search
USPC .............. 435/252.33, 106, 252.3, 320.1, 69.1
See application file for complete search history.

(56) References Cited

U.S. PATENT DOCUMENTS

| 4,278,765 | A | 7/1981 | Debabov et al. |
| 5,661,012 | A | 8/1997 | Sano et al. |
| 6,040,160 | A | 3/2000 | Kojima et al. |
| 2002/0037562 | A1 | 3/2002 | Livshits et al. |
| 2003/0157667 | A1 | 8/2003 | Vitushkina et al. |
| 2006/0057685 | A1 | 3/2006 | Stoynova et al. |
| 2009/0197309 | A1 | 8/2009 | Sycheva et al. |
| 2010/0099153 | A1 | 4/2010 | Vitushkina et al. |

FOREIGN PATENT DOCUMENTS

EP 1491634 12/2004

OTHER PUBLICATIONS

Yan et al Two-Amino Acid Molecular Switch in an Epithelial Morphogen That Regulates Binding to Two Distinct Receptors Science Oct. 20, 2000: vol. 290 No. 5491 pp. 523-527.*
Lecchi et al Identification of a new dysfunctional platelet P2Y12 receptor variant associated with bleeding diathesis Blood. 2015; 125(6):1006-1013).*
Alexander-Caudle, C., et al., "Acetohydroxy Acid Synthase Activity from a Mutation at ilvF in *Escherichia coli* K-12," J. Bacteriol. 1990;172(6):3060-3065.
Vinogradov, V., et al., "Acetohydroxyacid synthase isozyme I from *Escherichia coli* has unique catalytic and regulatory properties," Biochemica et Biophysica Acta 2006;1760;356-363.
Search Report from EP Patent App. No. 07017918.9 (Jun. 9, 2008).
Kopecký, J., et al., "Mutations in Two Distinct Regions of Acetolactate Synthase Regulatory Subunit from Streptomyces cinnamonensis Result in the Lack of Sensitivity to End-Product Inhibition," Biochem. Biophys. Res. Communications 1999;266:162-166.
Notice of Reason for Rejection issued in Japanese Patent App. No. 2007-237363 (Sep. 18, 2012) and English translation thereof.
Datsenko, K. A., et al., "One-step inactivation of chromosomal genes in *Escherichia coli* K-12 using PCR products," PNAS 2000;97(12):6640-6645.
De Felice, M., et al., "Growth Inhibition as a Consequence of Antagonism Between Related Amino Acids: Effect of Valine in *Escherichia coli* K-12," Microbiol. Rev. 1979;43(1):42-58.
Deuschle, U., et al., "Promoters of *Escherichia coli*: a hierarchy of in vivo strength indicates alternate structures," The EMBO Journal 1986;5(11):2987-2994.
Guardiola, J., et al., "The Acetolactate Synthase Isoenzymes of *Escherichia coli* K-12," Mol. Gen. Genet. 1977;156:17-25.
Karlin, S., et al., "Methods for assessing the statistical significance of molecular sequence features by using general scoring schemes," Proc. Natl. Acad. Sci. USA 1990;87:2264-2268.
Mendel, S., et al., "The N-terminal Domain of the Regulatory Subunit is Sufficient for Complete Activation of Acetohydroxyacid Synthase III from *Escherichia coli*," J. Mol. Biol. 2003;325:275-284.
Pearson, W. R., "Rapid and Sensitive Sequence Comparison with FASTP and FASTA," Methods in Enzymology 1990;183:63-98.
Shine, J., et al., "The 3'-Terminal Sequence of *Escherichia coli* 16S Ribosomal RNA: Complementarity to Nonsense Triplets and Ribosome Binding Sites," Proc. Natl. Acad. Sci. USA 1974;71(4):1342-1346.

(Continued)

*Primary Examiner* — Maria Leavitt
(74) *Attorney, Agent, or Firm* — Shelly Guest Cermak; Cermak Nakajima & McGowan LLP

(57) ABSTRACT

A mutant bacterial acetolactate synthase (AHAS I) which is resistant to feedback inhibition by L-valine is described. Also described is a method for producing branched-chain L-amino acids using a bacterium from the Enterobacteriaceae family wherein the L-amino acid productivity of said bacterium is enhanced by the use of the acetolactate synthase (AHAS I) which is resistant to feedback inhibition by L-valine. This acetolactate synthase contains a mutant small subunit encoded by the mutant ilvN gene.

10 Claims, 7 Drawing Sheets

(56) References Cited

OTHER PUBLICATIONS

Størmer, F. C., et al., "The Requirement for Flavine Adenine Dinucleotide in the Formation of Acetolactate by *Salmonella typhimurium* Extracts," Biochem. Biophys. Res. Comm. 1964;17(5):587-592.

Thompson, J. D., et al., "CLUSTAL W: improving the sensitivity of progressive multiple sequence alignment through sequence weighting, position-specific gap penalties and weight matrix choice," Nuc. Acids. Res. 1994;22 (22):4673-4680.

Weinstock, O., et al., "Properties of Subcloned Subunits of Bacterial Acetohydroxy Acid Synthases," J. Bacteriol. 1992;174(17):5560-5566.

Mendel, S., et al., "Acetohydroxyacid synthase: A proposed structure for regulatory subunits supported by evidence from mutagenesis1," Journal of Molecular Biology, vol. 307, Issue 1, Mar. 16, 2001, pp. 465-477.

Voet, Biochemistry, John Wiley and Sons, 1990, pp. 126-128.

Kimchi-Sarfaty, C., et al., "A "silent" polymorphism in the MDR1 gene changes substrate specificity," Science, Jan. 26, 2007;315(5811):525-528.

Rudinger, J., "Characteristics of the amino acids as components of a peptide hormone sequence," in Peptide Hormones, University Park Press: Baltimore, MD, pp. 1-7, 1976.

Ngo, J., et al., "Computational Complexity, Protein Structure Prediction, and the Levinthal Paradox," 1994, The Protein Folding Problem and Tertiary Structure Prediction, Merz et al. (eds.), Birkhauser Boston: Boston, MA, pp. 433 and 492-506.

* cited by examiner

Fig. 3

```
              M  Q  N  T  T  H  D  N  V  I  L  E  L  T  V  R  N  H  P  G
ilvN33  atgcaaaacacaactcatgacaacgtaattctggagctcaccgttcgcaaccatccgggc  60
        ::::::::::::::::::::::::::::::::::::::::::::::::::::::::::::
ilvN    atgcaaaacacaactcatgacaacgtaattctggagctcaccgttcgcaaccatccgggc  60
              M  Q  N  T  T  H  D  N  V  I  L  E  L  T  V  R  N  H  P  G
                                                                      20

40
              V  M  T  H  V  C  G  L  F  A  R  R  A  F  N  V  E  G  I  L
ilvN33  gtaatgacccacgtttgtggcctttttgcccgccgcgcttttaacgttgaaggcattctt  120
        ::::::::::::::::::::::::::::::::::::::::::::::::::::::::::::
ilvN    gtaatgacccacgtttgtggcctttttgcccgccgcgcttttaacgttgaaggcattctt  120
              V  M  T  H  V  C  G  L  F  A  R  R  A  F  N  V  E  G  I  L
                                                                      40
        ────────────────────────────────►
                        45
              C  L  P  R  F  &
ilvN33  tgtctgccgcgcttttaacgttgaaggcattctttgtctgccgattcaggacagcgacaa  180
        :::::                                   ::::::::::::::::::::
ilvN    tgtct---------------------------------gccgattcaggacagcgacaa  146
              C  L                                P  I  Q  D  S  D  K
                                                                      49 ilvN33  aagccatatctggctactggtcaatgacgaccagcgtctggagcagatgataagccaaat  240
        ::::::::::::::::::::::::::::::::::::::::::::::::::::::::::::
ilvN    aagccatatctggctactggtcaatgacgaccagcgtctggagcagatgataagccaaat  206
              S  H  I  W  L  L  V  N  D  D  Q  R  L  E  Q  M  I  S  Q  I
                                                                      69 ilvN33  cgataagctggaagatgtcgtgaaagtgcagcgtaatcagtccgatccgacgatgtttaa  300
        ::::::::::::::::::::::::::::::::::::::::::::::::::::::::::::
ilvN    cgataagctggaagatgtcgtgaaagtgcagcgtaatcagtccgatccgacgatgtttaa  266
              D  K  L  E  D  V  V  K  V  Q  R  N  Q  S  D  P  T  M  F  N
                                                                      89 ilvN33  caagatcgcggtgttttttcagtaa  325
        :::::::::::::::::::::::::
ilvN    caagatcgcggtgttttttcagtaa  291
              K  I  A  V  F  F  Q  &
                                   96
```

MUTANT ACETOLACTATE SYNTHASE AND A METHOD FOR PRODUCING BRANCHED-CHAIN L-AMINO ACIDS

This application is a Continuation of, and claims priority under 35 U.S.C. §120 to, U.S. patent application Ser. No. 11/854,601, filed on Sep. 13, 2007, now abandoned, which claimed priority under 35 U.S.C. §119 to Russian application 2006132818, filed on Sep. 13, 2006, the entireties of which are incorporated herein by reference. The Sequence Listing in electronic format filed herewith is also hereby incorporated by reference in its entirety (File Name: 2014-07-16T_US-345C_Seq_List; File Size: 17 KB; Date Created: Jul. 17, 2014).

BACKGROUND OF THE INVENTION

1. Field of the Invention

The present invention relates to biotechnology, and specifically to a method for producing branched-chain L-amino acids. More specifically, the present invention discloses the use of a new L-valine-resistant enzyme which is involved in the biosynthesis of branched-chain L-amino acids. More specifically, the present invention concerns a L-valine-resistant mutant acetolactate synthase (AHAS I) purified from *E. coli*, a bacteria from the Enterobacteriaceae family which contains this synthase enzyme, and a method for producing branched-chain L-amino acids by fermentation using the strains of this bacteria.

2. Brief Description of the Related Art

Traditionally, L-amino acids have been industrially produced by fermentation utilizing strains of microorganisms obtained from natural sources, or mutants thereof which have been specifically modified to enhance L-amino acid productivity.

Many techniques have been previously described to specifically enhance L-amino acid productivity, such as, for example, transformation of microorganisms with recombinant DNA (see, for example, U.S. Pat. No. 4,278,765). Such techniques are based on increasing the activities of the enzymes involved in amino acid biosynthesis and/or desensitizing the target enzymes to feedback inhibition by the produced L-amino acid (see, for example, Japanese Laid-open application No. 56-18596 (1981), WO 95/16042 or U.S. Pat. Nos. 5,661,012 and 6,040,160).

The biosynthesis of isoleucine, leucine, and valine occurs through a branched pathway in which three steps are common to each end product. The AHAS reaction represents the first biosynthetic step common to the three products. The reaction is catalyzed by isoenzymes which are the target of end-product inhibition by valine. This regulation plays a major role in the physiological control of the pathway in bacteria. The reaction includes condensation of active acetaldehyde (derived from pyruvate) with either α-ketobutyrate or pyruvate to yield α-aceto-α-hydroxybutyrate (a precursor of isoleucine) or α-acetolactate (a precursor of leucine and valine), respectively.

It has been reported that valine and its keto-acid precursor α-ketoisovaleric acid inhibit the growth of *E. coli* K12, and that isoleucine counters this inhibition (Tatum, E. L., Fed. Proc. 8:511 (1946)). At present, it is commonly accepted that inhibition of valine primarily results from blocking α-aceto-α-hydroxybutyrate synthesis. An analysis of *E. coli* K12 has revealed that this strain contains the structural genes for the three AHAS activities, which are designated as isoenzymes AHAS I, AHAS II, and AHAS III. AHAS I and AHAS III are both inhibited by valine, whereas AHAS II is resistant to it; however, AHAS II is not normally expressed in *E. coli* K12 cells (Guardiola, J. et al, Mol. Gen. Genet. 156:17-25 (1977)). All AHAS isozymes from enterobacteria are composed of a large and a small subunit in an $\alpha_2\beta_2$ structure, with the large subunits performing a catalytic function and the small subunits performing a regulatory function. The small subunits are absolutely required for sensitivity of the enzyme activity to the feedback inhibitor valine. A study of the individual properties of the AHAS I and AHAS III subunits (Weinstock O. et al, J. Bacteriol. 174:5560-5566 (1992)) showed that the small subunits specifically induced a catalytically competent conformation of the whole enzyme and stabilized the transition state.

On the basis of a model of the valine-binding region of the AHAS III regulatory small subunit from *E. coli*, truncations from the carboxyl end of the small subunit were made. These truncations induce a lack of valine sensitivity in the truncated AHAS III enzymes (Mendel S. et al, J Mol Biol. 10; 325(2): 275-84 (2003)).

But at present there are no reports describing mutant bacterial acetolactate synthase (AHAS I) which is feedback resistant to valine and the use of such a mutant acetolactate synthase for improving branched-chain L-amino acid production in corresponding L-amino acid producing strains.

SUMMARY OF THE INVENTION

The present invention provides a new mutant bacterial acetolactate synthase for the purpose of developing branched-chain L-amino acid-producing strains with enhanced productivity of branched-chain L-amino acids, and to provide a method for producing branched-chain L-amino acids using these strains.

The present invention was achieved by constructing a new mutant acetolactate synthase from *E. coli*. This mutant acetolactate synthase from *E. coli* has a mutation in the IlvN regulatory unit, specifically Asn-17, Ala-30, and/or Ile-44. This mutant acetolactate synthase was shown to enhance branched-chain L-amino acid production when DNA encoding the mutant enzyme is introduced into the branched-chain L-amino acid-producing strain.

It is an aspect of the present invention to provide a mutant bacterial acetolactate synthase (AHAS I) small subunit comprising the wild-type acetolactate synthase small subunit of *Escherichia coli* comprising a mutation selected from the group consisting of: replacing the L-amino acid at position 17 and/or 30 in said wild-type acetolactate synthase small subunit with another L-amino acid, replacing the N-terminus portion downstream from the L-amino acid at position 44 in said wild-type acetolactate synthase small subunit with several L-amino acids, and combinations thereof, wherein said mutant small subunit of acetolactate synthase is desensitized to feedback inhibition by valine.

It is a further aspect of the present invention to provide the mutant small subunit of bacterial acetolactate synthase (AHAS I) described above, wherein said L-amino acid at position 17 is replaced with a lysine residue.

It is a further aspect of the present invention to provide the mutant small subunit of bacterial acetolactate synthase (AHAS I) described above, wherein the L-amino acid at position 30 is replaced with a proline residue.

It is a further aspect of the present invention to provide the mutant small subunit of bacterial acetolactate synthase (AHAS I) described above, wherein said N-terminus portion downstream from the L-amino acid at position 44 is replaced with arginine and phenylalanine.

It is a further aspect of the present invention to provide the mutant small subunit of bacterial acetolactate synthase (AHAS I) described above, wherein said L-amino acid at position 17 which is replaced with a lysine residue is asparagine.

It is a further aspect of the present invention to provide the mutant small subunit of bacterial acetolactate synthase (AHAS I) described above, wherein said L-amino acid at position 30 which is replaced with a proline residue is alanine.

It is a further aspect of the present invention to provide the mutant small subunit of bacterial acetolactate synthase (AHAS I) described above, wherein said L-amino acid at position 44 which is replaced with arginine and phenylalanine is isoleucine.

It is a further aspect of the present invention to provide a mutant bacterial acetolactate synthase comprising the small subunit described above.

It is a further aspect of the present invention to provide the mutant acetolactate synthase described above, wherein said mutant acetolactate synthase comprises the *Escherichia coli* large subunit.

It is a further aspect of the present invention to provide the mutant bacterial acetolactate synthase described above, wherein the small subunit includes deletions, substitutions, insertions, or additions of one or several amino acids at one or more positions other than positions 17, 30 and/or 44, and wherein said mutant acetolactate synthase is desensitized to feedback inhibition by valine.

It is a further aspect of the present invention to provide a DNA coding for the mutant small subunit of the acetolactate synthase described above.

It is a further aspect of the present invention to provide a bacterium of the Enterobacteriaceae family, which contains the DNA described above and has the ability to produce branched-chain L-amino acids.

It is a further aspect of the present invention to provide the bacterium described above, wherein said branched-chain L-amino acids are selected from the group consisting of L-leucine, L-isoleucine, and L-valine.

It is a further aspect of the present invention to provide the bacterium described above, wherein the activity of the mutant acetolactate synthase is enhanced in the bacterium.

It is a further aspect of the present invention to provide the bacterium described above, wherein the bacterium belongs to the genus *Escherichia*.

It is a further aspect of the present invention to provide the bacterium described above, wherein the activity of the mutant acetolactate synthase is enhanced by increasing expression of the mutant acetolactate synthase gene.

It is a further aspect of the present invention to provide the bacterium described above, wherein the activity of the mutant acetolactate synthase is increased by a method selected from the group consisting of:

a) increasing the copy number the mutant acetolactate synthase gene,
b) modifying an expression control sequence of the gene so that the expression of the gene is enhanced, and
c) combinations thereof.

It is a further aspect of the present invention to provide the bacterium described above, wherein the copy number is increased by the integration of multiple copies of the mutant acetolactate synthase gene into the chromosome of the bacterium.

It is a further aspect of the present invention to provide a method for producing branched-chain L-amino acids comprising cultivating the bacterium described above in a culture medium, and collecting the branched-chain L-amino acids from the culture medium.

It is a further aspect of the present invention to provide the method described above, wherein the bacterium has enhanced expression of genes involved in branched-chain L-amino acid biosynthesis.

It is a further aspect of the present invention to provide the method described above, wherein said branched-chain L-amino acid is selected from the group consisting of L-leucine, L-isoleucine, and L-valine.

BRIEF DESCRIPTION OF THE DRAWINGS

FIG. 3 shows an alignment of the nucleotide and amino acid sequences of ilvN and ilvN33. The nucleotide sequence is shown in small letters, the amino acids in capital. A 34 bp direct repeat in ilvN33 is shown in bold and marked with arrows.

DESCRIPTION OF THE PREFERRED EMBODIMENTS

Figure 1:
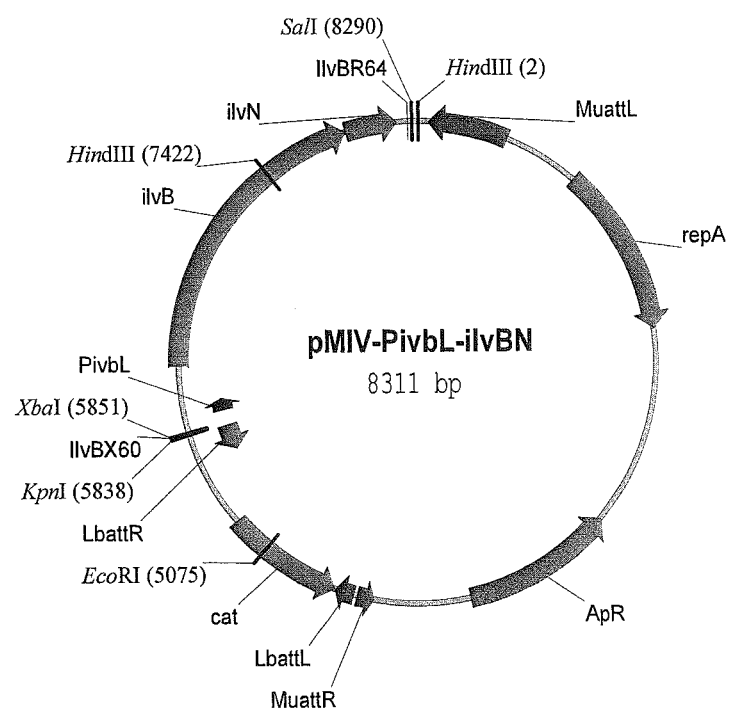
FIG. 1 shows the construction of the plasmid pMIV-P$_{ivbL}$-ilvBN.

Furthermore, the present invention will be explained in detail.

<1> The Mutant Small Subunit of Acetolactate Synthase and the Mutant Ilvn Gene

The term "bacterial acetolactate synthase" means the wild-type, or endogenous, acetolactate synthase present in bacteria of the Enterobacteriaceae family, corynebacteria, bacteria belonging to the genus *Bacillus* etc. The Enterobacteriaceae family includes bacteria belonging to the genera *Escherichia, Erwinia, Providencia*, and *Serratia*. The genus *Escherichia* is preferred.

The phrase "activity of acetolactate synthase" means the activity which catalyzes the formation of 2-aceto-2-hydroxybutyrate and $CO_2$ from pyruvate and 2-oxobutanoate, or the formation of 2-acetolactate and $CO_2$ from two molecules of pyruvate. This activity can be measured in bacterial extracts using the method of F. C. Stormer and H. E. Umbarger (Biochem. Biophys. Res. Commun., 17, 5, 587-592 (1964)).

Acetohydroxybutanoate synthase I, also called acetolactate synthase I (AHAS I) is a heterotetramer protein which includes two catalytic and two regulatory domains (Weinstock, O. et al, J. Bacteriol., 174(17), 5560-5566 (1992)). It is generally accepted that the large (ca. 60-kDa) subunits are catalytic, while the small ones are regulatory. AHAS I is coded for by the ilvB and ilvN genes.

Replacing the asparagine at position 17 and/or the alanine at position 30 in the small subunit of *Escherichia coli* acetolactate synthase [EC 4.1.3.18] with any amino acid, preferably lysine at position 17, and proline at position 30, results in a mutant protein which is resistant to feedback inhibition by valine. Also, replacing the N-terminus portion downstream from the L-amino acid at position 44 with one or several amino acids, preferably 2 amino acids such as arginine and phenylalanine, results in a mutant protein which is resistant to feedback inhibition by valine. A typical example of such a mutant is IlvN33 (SEQ ID NO: 11). Several amino acids can be replaced downstream of position 44, but typically can be between 1 to 20, preferably 1 to 10, and more preferably 2. The small subunit of the wild-type acetolactate synthase which has a substitution(s) at position 17, and/or position 30, or has several amino acids replaced in the N-terminus portion downstream from position 44, may be referred to as the "mutant small subunit". The acetolactate synthase containing the mutant small subunit may be referred to as the "mutant acetolactate synthase". A DNA coding for the mutant small subunit may be referred to as the "mutant ilvN gene". The small subunit of acetolactate synthase without any substitutions may be referred to as "a wild-type small subunit". An acetolactate synthase which contains wild-type small subunits may be referred to as "a wild-type acetolactate synthase". Furthermore, a DNA encoding the mutant small subunit of the present invention and a large subunit of acetolactate synthase may be referred to as the "mutant acetolactate synthase gene".

The ilvB gene (synonym—b3671) encodes the acetolactate synthase large subunit. The ilvB gene (nucleotides complementary to nucleotide positions 3849119 to 3850807; GeneBank accession no. NC_000913.2; gi:16129170) is located between the ilvN gene and ivbL gene on the chromosome of *E. coli* K-12.

The ilvN gene (synonym—b3670) encodes the acetolactate synthase small subunit. The ilvN gene (nucleotides complementary to nucleotide positions 3848825 to 3849115; GeneBank accession no. NC_000913.2; gi:49175990) is located between the uhpA and ilvB genes on the chromosome of *E. coli* K-12. The nucleotide sequence of the ilvN gene and the amino acid sequence of the acetolactate synthase small subunit encoded by the ilvN gene are shown in SEQ ID NO: 1 and SEQ ID NO: 2, respectively. The ilvB and ilvN genes forms the ilvBN operon.

The mutant small subunit is obtained by introducing mutations into a wild-type ilvN gene using known methods. The ilvBN operon can be obtained by PCR (polymerase chain reaction; refer to White, T. J. et al., Trends Genet., 5, 185 (1989)) utilizing primers based on the nucleotide sequence of the operon. Genes coding for acetolactate synthase from other microorganisms can be obtained in a similar manner.

The mutant small subunit may include deletions, substitutions, insertions, or additions of one or several amino acids at one or more positions other than 17, 30, and/or 44, provided that the activity of acetolactate synthase which contains the mutant subunits is maintained. The number of "several" amino acids differs depending on the position in the three dimensional structure of the protein or the type of amino acid residues. This is because some amino acids are similar to one another in their structure and function within a protein, and interchanging of such amino acids does not greatly affect the three dimensional structure or the function of the protein. Therefore, the mutant acetolactate synthase of the present invention may be one which has homology of not less than 70%, preferably 80%, and more preferably 90%, and most preferably 95% with respect to the entire amino acid sequence for acetolactate synthase, and which maintains the acetolactate synthase activity. Alternatively, the number of "several" amino acids may be 1 to 30, preferably 1 to 15, and more preferably 1 to 5.

The substitutions, deletions, insertions or additions of one or several amino acid residues is/are conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The large subunit of the acetolactate synthase encoded by the ilvB gene also may include deletions, substitutions, insertions, or additions of one or several amino acids at one or more positions.

In the present invention, the phrase "L-amino acid at position 17, 30, and/or 44" means an amino acid residue corresponding to the amino acid residue at position 17, 30, and/or 44 in the amino acid sequence of SEQ ID NO: 2, which is the sequence of the *E. coli* wild-type small subunit of acetolactate synthase. In the small subunit of the acetolactate synthase from *E. coli*, the amino acid residue in position 17 is asparagine, the amino acid residue in position 30 is alanine, and the amino acid residue in position 44 is isoleucine. The position of an amino acid residue may change. For example, if an amino acid residue is inserted at the N-terminus portion, the amino acid residue at position 17, 30, and/or 44 becomes position 18, 31, and/or 45. In such a case, the amino acid residue at the original position 17, 30, and/or 44 is designated as the amino acid residue at the position 17, 30 and/or 44 in the present invention.

To determine the L-amino acid at position 17, 30, and/or 44 of a small subunit of acetolactate synthase from a bacterium of interest, the amino acid sequence of the small subunit of the acetolactate synthase from *E. coli* (SEQ ID NO: 2) is aligned with the amino acid sequence of the small subunit of the acetolactate synthase from the bacterium of interest, and the L-amino acids at positions 17, 30 and/or 44 in the small subunit of the acetolactate synthase from the bacterium of interest can be determined.

The DNA which codes for substantially the same protein as the mutant small subunit described above is obtained, for example, by modifying the nucleotide sequence by site-directed mutagenesis so that one or more amino acid residues at a specified site are deleted, substituted, inserted, or added. DNA modified as described above is obtained by conventionally known mutation treatments. Such mutation treatments include treating a DNA containing the mutant ilvN gene in vitro, for example, with hydroxylamine, and treating a microorganism, for example, a bacterium belonging to the genus *Escherichia* harboring the mutant ilvN gene, with ultraviolet irradiation or a known mutating agent such as N-methyl-N'-nitro-N-nitrosoguanidine (NTG) and nitrous acid.

The substitutions, deletions, insertions, or additions of nucleotides as described above also include naturally occurring mutations (mutant or variant), for example, on the basis of individual differences or differences in species or genus of the bacterium which contains acetolactate synthase.

The DNA which codes for substantially the same protein as the mutant small subunit can be obtained by isolating a DNA which hybridizes with DNA having a sequence complimentary to the known ilvN gene sequence or part of it under stringent conditions, and which codes for a protein which forms a whole enzyme having acetolactate synthase activity with a large subunit, from a cell which is has been subjected to mutation treatment.

"Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected depending on the hybridization conditions, and is usually 100 bp to 1 kbp.

To evaluate the degree of protein or DNA homology, several calculation methods, such as a BLAST search, FASTA search, and ClustalW, can be used.

BLAST (Basic Local Alignment Search Tool) is the heuristic search algorithm employed by the programs blastp, blastn, blastx, megablast, tblastn, and tblastx. These programs ascribe significance to their findings using the statistical methods of Karlin, Samuel and Stephen F. Altschul ("Methods for assessing the statistical significance of molecular sequence features by using general scoring schemes". Proc. Natl. Acad. Sci. USA, 1990, 87:2264-68; "Applications and statistics for multiple high-scoring segments in molecular sequences". Proc. Natl. Acad. Sci. USA, 1993, 90:5873-7). The FASTA search method is described by W. R. Pearson ("Rapid and Sensitive Sequence Comparison with FASTP and FASTA", Methods in Enzymology, 1990 183:63-98). The ClustalW method is described by Thompson J. D., Higgins D. G. and Gibson T. J. ("CLUSTAL W: improving the sensitivity of progressive multiple sequence alignment through sequence weighting, position-specific gap penalties and weight matrix choice", Nucleic Acids Res. 1994, 22:4673-4680).

The gene which is able to hybridize under the conditions as described above, includes genes which have a stop codon within the coding region, and genes which are inactive due to mutation of the active site. However, such inconveniences can be easily removed by ligating the gene with a commercially available expression vector, and investigating the acetolactate synthase activity of whole enzyme containing the expressed protein.

<2> Bacterium of the Present Invention

The bacterium of the present invention is a branched-chain L-amino acid-producing bacterium of the Enterobacteriaceae family which contains a DNA which codes for the mutant small subunit of acetolactate synthase. Furthermore, the bacterium of the present invention is a branched-chain L-amino acid-producing bacterium of the Enterobacteriaceae family which has increased mutant acetolactate synthase activity. Specifically, the bacterium of the present invention is a branched-chain L-amino acid-producing bacterium of the Enterobacteriaceae family, wherein branched-chain L-amino acid production is increased due to the introduction into the bacterium of the mutant ilvN gene which encodes the mutant small subunit of the present invention. The bacterium of the present invention is a branched-chain L-amino acid-producing bacterium belonging to the genus Escherichia, wherein branched-chain L-amino acid production is increased by enhancing the activity of acetolactate synthase, namely valine-resistant mutant acetolactate synthase, in the bacterium. More concretely, the bacterium of present invention contains the mutant ilvN gene on the bacterial chromosome or in a plasmid, wherein the gene is over-expressed, and this bacterium has an enhanced ability to produce branched-chain L-amino acids.

The phrase "bacterium which has the ability to produce branched-chain L-amino acids" indicates a bacterium which has the ability to cause accumulation of branched-chain L-amino acids in a medium, such as L-leucine, L-isoleucine and L-valine, when the bacterium of the present invention is cultured in the medium. The branched-chain L-amino acid producing ability may be imparted or enhanced by breeding. The phrase "bacterium which has an ability to produce branched-chain L-amino acid" used herein also indicates a bacterium which is able to produce and cause accumulation in the culture medium of a larger amount of branched-chain L-amino acids than a wild-type or parental strain, and preferably means that the bacterium is able to produce and cause accumulation in the medium of not less than 0.5 g/L, more preferably not less than 1.0 g/L of the branched-chain L-amino acids. Exemplary L-amino acids include L-leucine, L-isoleucine, and L-valine.

The Enterobacteriaceae family includes bacteria belonging to the genera Escherichia, Enterobacter, Erwinia, Klebsiella, Pantoea, Photorhabdus, Providencia, Salmonella, Serratia, Shigella, Morganella and Yersinia, etc. Specifically, those classified as Enterobacteriaceae according to the taxonomy used in the NCBI (National Center for Biotechnology Information) database (http://www.ncbi.nlm.nih.gov/Taxonomy/Browser/wwwtax.cgi?id=91347) can be used. A bacterium belonging to the genus Escherichia or Pantoea is preferred.

The term "a bacterium belonging to the genus Escherichia" means the bacterium classified as the genus Escherichia according to the classification known to a person skilled in the microbiology. An example is Escherichia coli (E. coli).

The phrase "activity of the mutant acetolactate synthase is enhanced" means that the activity per cell is higher than that of a non-modified strain, for example, a wild-type strain. Exemplary enhanced activities include when the number of the mutant acetolactate synthase molecules per cell increases, and when the specific activity per mutant acetolactate synthase molecule increases, and so forth. Furthermore, an exemplary wild-type strain that may be used for comparison, for example, is Escherichia coli K-12. As a result of enhancing the intracellular activity of the mutant acetolactate synthase, the amount of branched chain L-amino acids in the medium is increased.

The mutant acetolactate synthase activity in a bacterial cell can be enhanced by increasing the expression of the gene coding for the mutant acetolactate synthase. Any gene which codes for mutant acetolactate synthase derived or isolated from bacteria of the Enterobacteriaceae family or coryneform bacteria can be used. Among these, genes derived from bacteria belonging to the genus Escherichia are preferred.

Transforming a bacterium with a DNA coding for a protein means introducing the DNA into a bacterium cell, for example, by conventional methods, to increase the expression of the gene coding for the protein of present invention and to enhance the activity of the protein in the bacterial cell.

Methods for enhancing gene expression include increasing the gene copy number. Introducing a gene into a vector that is able to function in a bacterium belonging to the genus Escherichia increases the copy number of the gene. For such purposes, multi-copy vectors can be preferably used, such as pBR322, pUC19, pBluescript KS+, pACYC177, pACYC184, pAYC32, pMW119, pET22b, or the like. Gene expression can also be enhanced by introducing multiple copies of the gene into the bacterial chromosome by, for example, homologous recombination, or the like.

Gene expression can also be enhanced by placing the DNA of the present invention under the control of a promoter which is stronger than the native promoter. The strength of a promoter is defined by the frequency of RNA synthesis initiation. Methods for evaluating the strength of a promoter and examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5, 2987-2994). For example, the $P_R$ promoter is known as a potent constitutive promoter. Other known potent promoters are the $P_L$ promoter, lac promoter, trp promoter, trc promoter, of lambda phage, and the like.

Translation can be enhanced by introducing into the DNA of the present invention a more efficient Shine-Dalgarno sequence (SD sequence) in the place of the native SD sequence, when the SD sequence is upstream of the start codon of the mRNA which interacts with the 16S RNA of ribosome (Shine J. and Dalgarno L., Proc. Natl. Acad. Sci. USA, 1974, 71, 4, 1342-6).

Using a potent promoter can be combined with using multiple gene copies.

Methods for preparing chromosomal DNA, hybridization, PCR, preparation of plasmid DNA, digestion and ligation of DNA, transformation, selection of an oligonucleotide as a primer, and the like may be typical methods which are well known to one skilled in the art. These methods are described in Sambrook, J., and Russell D., "Molecular Cloning A Laboratory Manual, Third Edition", Cold Spring Harbor Laboratory Press (2001), and the like.

The bacterium of the present invention can be obtained by introducing the aforementioned DNAs into a bacterium which inherently is able to produce branched-chain L-amino acids. Alternatively, the bacterium of present invention can be obtained by imparting the ability to produce branched-chain L-amino acid to a bacterium already containing the DNAs.

For the parent strain of the present invention, L-valine producing bacteria belonging to the genus *Escherichia* such as H-81 (VKPM B-8066), NRRL B-12287 and NRRL B-12288 (U.S. Pat. No. 4,391,907), VKPM B-4411 (U.S. Pat. No. 5,658,766), VKPM B-7707 (European patent application EP1016710A2), or the like is employed. Also, L-leucine producing bacteria belonging to the genus *Escherichia* may be used, such as H-9070 (FERM BP-4704) and H-9072 (FERM BP-4706) (U.S. Pat. No. 5,744,331), VKPM B-7386 and VKPM B-7388 (RU2140450), W1485atpA401/pMWdAR6, W1485lip2/pMWdAR6 and AJ12631/pMWdAR6 (EP0872547), or the like. Also, L-isoleucine producing bacteria belonging to the genus *Escherichia* may be used, such as strain (NZ10) TDH6/pVIC40, pMWD5 (Hashiguchi, K. et al, Biosci. Biotechnol. Biochem., 63(4), 672-679 (1999)), or strain AJ12919 described in European patent application EP 685555 A1, or the like.

<3> Method of the Present Invention

The method of present invention includes producing a branched-chain L-amino acid, such as L-leucine, L-isoleucine, and L-valine, by cultivating the bacterium of the present invention in a culture medium, allowing the branched-chain L-amino acid to be produced in the culture medium, and collecting the branched-chain L-amino acid from the culture medium.

In the present invention, the cultivation, the collection and purification of branched-chain L-amino acids from the medium and the like may be performed in a manner similar to conventional fermentation methods wherein an amino acid is produced using a microorganism. The medium used for culture may be either synthetic or natural, so long as it includes a carbon source and a nitrogen source and minerals and, if necessary, appropriate amounts of nutrients which the microorganism requires for growth. The carbon source may include various carbohydrates such as glucose and sucrose, and various organic acids. Depending on the mode of assimilation of the chosen microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium chloride, and the like, are used. Additional nutrients can be added to the medium if necessary. For instance, if the microorganism requires proline for growth (proline auxotrophy) a sufficient amount of proline can be added to the medium.

The cultivation is performed preferably under aerobic conditions such as a shaking culture, and a stirring culture with aeration, at a temperature of 20 to 42° C., preferably 37 to 40° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by ion-exchange, concentration, and crystallization methods.

EXAMPLES

The present invention will be more concretely explained below with reference to the following non-limiting Examples.

Example 1

Cloning of ilvBN Operon Encoding AHAS I of *E. coli*

The ilvBN operon was cloned into the pMIV5JS vector as a part of a 2439 bp PCR product. Construction of the vector pMIV5JS is described below in Reference example 1. The MG1655 chromosome was used as a template in the PCR reaction. Synthetic oligonucleotides ilvBX60 (SEQ ID NO: 3) and ilvBR64 (SEQ ID NO: 4) were used as primers. Primer ilvBX60 contains the XbaI-restriction site at the 5'-end, and primer ilvBR64 contains the SalI-restriction site at the 5'-end. Conditions for PCR were the following: denaturation for 5 min at 94° C.; profile for 30 cycles: 30 sec at 94° C., 30 sec at 59° C., 2 min at 72° C.; final step: 7 min at 72° C. The 2449 bp PCR product was purified in an agarose gel, treated with XbaI and SalI, and cloned into the pMIV5JS vector which had been treated with the same restrictases. The strain B7ΔilvBNΔilvGMΔilvIH was used as the recipient for cloning. Construction of the strain B7ΔilvBNΔilvGMΔilvIH is described below in Reference example 2. The resulting plasmid pMIV-P$_{ivbL}$-ilvBN (FIG. 1) complemented the AHAS⁻ phenotype of the B7ΔilvBNΔilvGMΔilvIH strain.

Example 2

Breeding of Valine-Resistant Mutants of E. coli Acetolactate Synthase Isoform I (IlvBN$^{ValR}$)

The strain B7ΔilvBNΔilvGMΔilvIH/pMIV-P$_{ivbL}$-ilvBN described in Example 1 contains only one operon encoding AHAS (ilvBN operon). Spontaneous mutants resistant to valine were selected on plates with minimal medium and supplemented with 1 g/l of valine. Acetolactate synthase activity and enzymes resistance to L-valine inhibition were determined in crude extracts by the method of F. C. Stomer and H. E. Umbarger (Biochem. Biophys. Res. Commun., 17, 5, 587-592 (1964)). For the crude extracts, cells were grown in M9 minimal medium up to the end of the logarithmic phase, washed with 100 mM KH$_2$PO$_4$/K$_2$HPO$_4$ buffer supplemented with 100 mM KCl, pH 7.0. The crude cellular extracts were prepared by sonication of the cells in the same buffer. Plasmids isolated from the selected valine-resistant mutants were used for re-transformation of the AHAS-deficient strain B7ΔilvBNΔilvGMΔilvIH. As a result, the plasmid pMIV-P$_{ivbL}$-ilvBN$^{ValR33}$ was obtained, which provided valine-resistant growth of the AHAS-deficient recipient strain. This plasmid contains an operon encoding AHAS I resistant to valine inhibition. Residual AHAS activity in the presence of 10 mM L-valine was measured. Residual AHAS activity is equal to the activity in the presence of L-valine (nmol/min mg)*100%/the activity in the absence of L-valine (nmol/min mg). AHAS activity was measured by the method of F. C. Stormer and H. E. Umbarger (Biochem. Biophys. Res. Commun., 17, 5, 587-592 (1964)). Results of AHAS activity measurements for this strain are presented in Table 1.

Example 3

Nucleotide Sequence of the Gene Encoding Valine Resistant AHAS I

Figure 2:
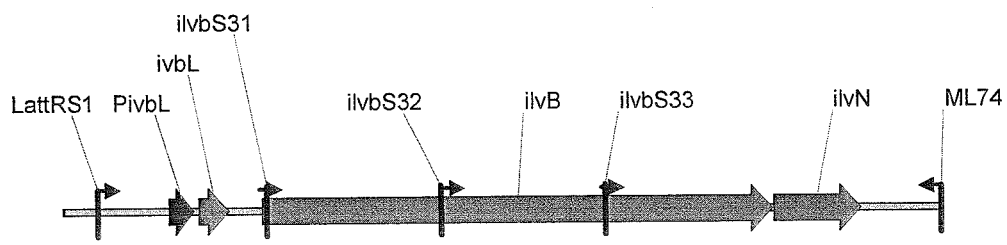
FIG. 2 shows the strategy for sequencing the ilvBN33 operon.

Five oligonucleotides were used to sequence the ilvBN DNA fragment cloned in pMIV-P$_{ivbL}$-ilvBN33: ML74 (SEQ ID NO: 5), LattRS1 (SEQ ID NO: 6), ilvBS31 (SEQ ID NO: 7), ilvBS32 (SEQ ID NO: 8), and ilvBS33 (SEQ ID NO: 9). The sequencing strategy is presented in FIG. 2

The resulting sequence is shown as ilvBN33 (SEQ ID NO: 10) in the Sequence listing. Comparison of this sequence with calculating programs revealed a direct repeat of 34 nucleotides in the region coding for the small subunit. The mutant gene was named ilvN33 (FIG. 3). This DNA rearrangement lead to earlier translation termination, resulting in replacement of the N-terminus portion downstream from the isoleucine at position 44 with arginine and phenylalanine, which forms the 45 amino acid truncated protein IlvN33 (SEQ ID NO: 11).

Example 4

Integration of the P$_{ivbL}$-ilvBN$^{ValR33}$ Operon into the Chromosome of the AHAS Deficient Strain, Followed by Elimination of the Cat Marker 1. Integration of Cat-P$_{ivbL}$-ilvBN$^{ValR33}$ Genes into the Chromosome To integrate mini-Mu::cat-P$_{ivbL}$-ilvBN$^{ValR33}$ into the bacterial chromosome, standard procedures were used. pMIV-P$_{ivbL}$-ilvBN$^{ValR33}$ was introduced into the B7ΔilvBNΔilvGMΔilvIH/pMH10 cells. Mu transposase encoded by pMH10 (pACYC177 derivative harboring Km$^R$ gene, Mu-phage A and B genes encoding Mu transposase, cts62 gene encoding Mu repressor, and the phage-lambda repressor gene c1857) (European patent EP1149911) was induced by incubating for 20 min at 44° C. immediately after the transformation.

Chloramphenicol resistant (Cm$^R$) clones were selected at 30° C. on LB agar plates containing 20 mg/l chloramphenicol. After eliminating both plasmids by cultivation of these clones in LB, Cm$^R$Km$^S$Ap$^S$ clones were obtained which were able to grow on minimal medium without additions.

As a result, the strain B7ΔilvBNΔilvGMΔilvIH mini-Mu::cat-P$_{ivbL}$-ilvBN$^{ValR33}$ containing the integrated cassette mini-Mu::cat-P$_{ivbL}$-ilvBN$^{ValR33}$ in a non-identified chromosomal locus was obtained.

2. Elimination of the Chloramphenicol Resistance Marker from Strain B7ΔilvBNΔilvGMΔilvIH Mini-Mu::Cat-P$_{ivbL}$-ilvBN$^{ValR33}$ To eliminate the chloramphenicol resistance marker from B7ΔilvBNΔilvGMΔilvIH, mini-Mu::cat-P$_{ivbL}$-ilvBN$^{ValR33}$ cells were transformed with the plasmid pMW118-int-xis (Ap$^R$) (WO2005/010175). Ap$^R$ clones were grown on LB agar plates containing 150 mg/l ampicillin at 30° C. Several tens of Ap$^R$ clones were picked up and tested for chloramphenicol sensitivity. The plasmid pMW118-int-xis was eliminated from Cm$^S$ cells by incubation on LB agar plates at 42° C. As a result, the strain B7ΔilvBNΔilvGMΔilvIH mini-Mu::P$_{ivbL}$-ilvBN$^{ValR33}$ containing the integrated cassette mini-Mu::P$_{ivbL}$-ilvBN$^{ValR33}$ in a non-identified chromosomal locus was obtained. Residual AHAS activity in the presence of 10 mM L-valine was measured. Results of AHAS activity measurements for this strain are presented in Table 1.

Example 5

Replacing the Native Promoter of ilvBN$^{ValR33}$ Operon with an Artificial Regulator Region 1. Modification of the Regulator Region of the ilvBN$^{ValR33}$ Operon Modifying the regulator region of the ilvBN$^{ValR33}$ operon, namely replacing the native promoter region of the ilvBN operon with the P$_L$ promoter, was accomplished by the method first developed by Datsenko and Wanner (Proc. Natl. Acad. Sci. USA, 2000, 97(12), 6640-6645) called "Red-driven integration". According to this procedure, the PCR primers ilvB-attR1 (SEQ ID NO: 12) and ilvB-PLSD (SEQ ID NO:13) were constructed. Oligonucleotide ilvB-attR1 (SEQ ID NO: 12) is homologous to the region upstream of the ilvB gene and the region adjacent to the gene conferring antibiotic resistance present in the chromosomal DNA of BW25113 cat-P$_L$-yddG. Oligonucleotide ilvB-PLSD (SEQ ID NO: 13) is homologous to both the ilvB region and the region downstream to the P$_L$ promoter present in the chromosome of BW25113 cat-P$_L$-yddG. Obtaining BW25113 cat-P$_L$-yddG has been described in detail (EP1449918A1, Russian patent RU2222596). The chromosomal DNA of strain BW25113 cat-P$_L$-yddG was used as a template for PCR. Conditions for PCR were the following: denaturation for 3 min at 95° C.; profile for two first cycles: 1 min at 95° C., 30 sec at 34° C., 40 sec at 72° C.; profile for the last 30 cycles: 30 sec at 95° C., 30 sec at 50° C., 40 sec at 72° C.; final step: 5 min at 72° C. As a result, the PCR product was obtained (SEQ ID NO: 14), purified in agarose gel, and used for electroporation of the E. coli strain B7ΔilvBNΔilvGMΔilvIH mini-Mu::

P$_{ivbL}$-ilvBN$^{ValR33}$, which contains the plasmid pKD46 with a temperature-sensitive replication origin. The plasmid pKD46 (Datsenko and Wanner, Proc. Natl. Acad. Sci. USA, 2000, 97:12:6640-45) includes the 2,154 nt (31088-33241) DNA fragment of phage λ (GenBank accession No. J02459), containing the genes of the λ Red homologous recombination system (γ, β, exo genes) under the control of the arabinose-inducible P$_{araB}$ promoter. The plasmid pKD46 is necessary for integration of the PCR product into the chromosome of the strain B7ΔilvBNΔilvGMΔilvIH mini-Mu::P$_{ivbL}$-ilvBN$^{ValR33}$.

Electrocompetent cells were prepared as follows: *E. coli* strain B7ΔilvBNΔilvGMΔilvIH mini-Mu::P$_{ivbL}$-ilvBN$^{ValR33}$ was grown overnight at 30° C. in LB medium containing ampicillin (100 mg/l), and the culture was diluted in 100 times with 5 ml of SOB medium (Sambrook et al, "Molecular Cloning A Laboratory Manual, Second Edition", Cold Spring Harbor Laboratory Press (1989)) with ampicillin and L-arabinose (1 mM). The cells were grown with aeration at 30° C. to an OD$_{600}$ of ≈0.6 and then made electrocompetent by concentrating 100-fold and washing three times with ice-cold deionized H$_2$O. Electroporation was performed using 70 μl of cells and ≈100 ng of PCR product. Following electroporation, the cells were incubated with 1 ml of SOC medium (Sambrook et al, "Molecular Cloning A Laboratory Manual, Second Edition", Cold Spring Harbor Laboratory Press (1989)) at 37° C. for 2.5 h, plated onto L-agar, and grown at 37° C. to select Cm$^R$ recombinants. Then, to eliminate the pKD46 plasmid, 2 passages on L-agar with Cm at 42° C. were performed and the resulting colonies were tested for sensitivity to ampicillin.

2. Verification of the ilvBN Regulator Region Modification

The clone B7ΔilvBNΔilvGMΔilvIH mini-Mu::cat-P$_L$-ilvBN$^{ValR33}$ was obtained, which contains the cassette mini-Mu::cat-P$_L$-ilvBN$^{ValR33}$ with the mutant ilvBN$^{ValR33}$ operon encoding the feedback-resistant AHAS I under the control of the phage lambda P$_L$ promoter, marked with Cm resistance gene. The replacement of the native ilvBN regulator region with the P$_L$ promoter, marked with the Cm resistance gene, was verified by PCR. Phage Mu right attachment-specific primer MR74 (SEQ ID NO: 15) and the primer specific to chloramphenicol acetyltransferase gene Cm-test2 (SEQ ID NO: 16) were used in PCR for the verification. Conditions for PCR verification were the following: denaturation for 3 min at 94° C.; profile for the 30 cycles: 30 sec at 94° C., 30 sec at 55° C., 1 min at 72° C.; final step: 7 min at 72° C. The PCR product obtained using the cells of B7ΔilvBNΔilvGMΔilvIH mini-Mu::cat-P$_{ivbL}$-ilvBN$^{ValR33}$ as a template was 586 nt in length (SEQ ID NO: 17). The PCR product obtained using the cells of B7ΔilvBNΔilvGMΔilvIH mini-Mu::cat-P$_L$-ilvBN$^{ValR33}$ as a template was 879 nt in length (SEQ ID NO: 18). Residual AHAS activity in the B7ΔilvBNΔilvGMΔilvIH mini-Mu::cat-P$_L$-ilvBN$^{ValR33}$ strain in the presence of 10 mM L-valine was measured. Results of AHAS activity measurements for this strain are presented in Table 1.

TABLE 1

| Strain | AHAS activity, nmol/min mg | Residual AHAS activity in presence of 10 mM L-Val, % |
| --- | --- | --- |
| B7ΔilvBNΔilvGMΔilvIH | 0 | 0 |
| B7ΔilvBNΔilvGMΔilvIH/pMIV-P$_{ivbL}$-ilvBN | 8.1 | 11 |
| B7ΔilvBNΔilvGMΔilvIH/pMIV-P$_{ivbL}$-ilvBN$^{ValR33}$ | 1.3 | 92 |

TABLE 1-continued

| Strain | AHAS activity, nmol/min mg | Residual AHAS activity in presence of 10 mM L-Val, % |
| --- | --- | --- |
| B7ΔilvBNΔilvGMΔilvIH mini-Mu::P$_{ivbL}$-ilvBN$^{ValR33}$ | 1.7 | 82 |
| B7ΔilvBNΔilvGMΔilvIH mini-Mu::cat-P$_L$-ilvBN$^{ValR33}$ | 21.5 | 91 |

Example 6

Production of L-Valine by the *E. coli* Strains with Valine-Resistant AHAS I

Both *E. coli* strains B7ΔilvBNΔilvGMΔilvIH mini-Mu::P$_{ivbL}$-ilvBN$^{ValR33}$ and B7ΔilvBNΔilvGMΔilvIH mini-Mu::cat-P$_L$-ilvBN$^{ValR33}$ were grown for 18 hours at 37° C. on L-agar plates. Then, cells from about 0.5 cm$^2$ of the plate surface were introduced into the fermentation medium (2 ml) and cultivated in tubes with aeration for 72 hours at 32° C. For the auxotrophic AHAS-deficient strain B7ΔilvBNΔilvGMΔilvIH, the fermentation medium was additionally supplemented with 100 μg/ml each of isoleucine and valine. The accumulated L-valine was measured by TLC. The results are presented in Table 2.

The composition of the fermentation medium (g/l):

| | |
| --- | --- |
| Glucose | 60.0 |
| (NH$_4$)$_2$SO$_4$ | 18.0 |
| KH$_2$PO$_4$ 3H$_2$O | 2.0 |
| MgSO$_4$ 7H$_2$O | 1.0 |
| CaCO$_3$ | 25.0 |
| Thiamin | 0.02 |
| Mameno | 4.0 |

TABLE 2

| Strain | L-valine, g/l |
| --- | --- |
| B7 | 0 |
| B7ΔilvBNΔilvGMΔilvIH | 0 |
| B7ΔilvBNΔilvGMΔilvIH mini-Mu::P$_{ivbL}$-ilvBN$^{ValR33}$ | 2.0 |
| B7ΔilvBNΔilvGMΔilvIH mini-Mu::cat-P$_L$-ilvBN$^{ValR33}$ | 3.0 |

As shown in Table 2, expression of valine-resistant AHAS I resulted in the production of valine. Operon P$_{ivbL}$-ilvBN$^{ValR33}$ is controlled by transcription attenuation and cyclic-AMP. Replacement of the native regulator region of the ilvBN$^{ValR33}$ operon (including elimination of the gene (ivbL) encoding the leader peptide) in *E. coli* strain B7ΔilvBNΔilvGMΔilvIH mini-Mu::P$_{ivbL}$-ilvBN$^{ValR33}$ with the P$_L$ promoter of phage lambda increased the production of L-valine by 1.5 times.

Example 7

New *E. coli* AHAS I Valine-Resistant Mutants with Modified ilvBN Expression

The native regulator region of the ilvBN operon was replaced with the phage lambda P$_L$ promoter by the same method as described in Example 5 in strain B7 ΔilvIH ΔilvGM (see Reference Example 2, section 5). This strain has only AHAS I. The resulting strain B7 ΔilvIH ΔilvGM cat-P$_L$- ilvBN was sensitive to valine. New valine-resistant spontaneous mutants of AHAS I were obtained from this strain. Strains which grew better on 1 g/l of valine were characterized (Table 3).

TABLE 3

| Strain | AHAS specific activity, nmol/min mg | Residual activity (%) in the presence of 10 mM of L-valine | L-isoleucine |
|---|---|---|---|
| B7 ΔilvIH ΔilvGM cat-$P_L$-ilvBN ValR1 | 40 | 86 | 91 |
| B7 ΔilvIH ΔilvGM cat-$P_L$-ilvBN ValR4 | 88 | 74 | 87 |
| B7 ΔilvIH ΔilvGM cat-$P_L$-ilvBN ValR5 | 72 | 86 | 98 |
| B7 ΔilvIH ΔilvGM cat-$P_L$-ilvBN ValR6 | 39 | 54 | 90 |
| B7 ΔilvIH ΔilvGM cat-$P_L$-ilvBN ValR18 | 57 | 97 | 94 |
| B7 ΔilvIH ΔilvGM cat-$P_L$-ilvBN (wt) | 49 | 15 | 22 |
| B7ΔilvBNΔilvGMΔilvIH mini-Mu::cat-$P_L$-ilvBN33 | 9 | 86 | 100 |

Valine-resistant mutations which were resistant to isoleucine were obtained, as well. Variants with a specific activity higher than that of the wild-type were obtained. As seen in Table 4, expression of valine-resistant AHAS I resulted in the production of valine. The fermentation medium contained 6% glucose. The nucleotide sequences of the mutant operons for the two best mutants, ilvBNValR1 and ilvBNValR4, were determined. It was revealed that IlvBN ValR1 contained one point mutation in INN: A30P Ala-Pro (Ala at position 30 is replaced with Pro; corresponding codon gcc was replaced with ccc), and IlvBNValR4 also contained one point mutation in IlvN: N17K Asn-Lys (Asn at position 17 is replaced with Lys; corresponding codon aac was replaced with aag). In both cases, such substitutions were rare.

TABLE 4

| Strain | L-valine, g/l |
|---|---|
| B7ΔilvIHΔilvGM cat-$P_L$-ilvBN ValR1 | 2.3 |
| B7ΔilvIHΔilvGM cat-$P_L$-ilvBN ValR4 | 7.6 |
| B7ΔilvIHΔilvGM cat-$P_L$-ilvBN ValR5 | 3.3 |
| B7ΔilvIHΔilvGM cat-$P_L$-ilvBN wt | 0 |

Example 8

Production of L-Leucine by the *E. coli* Strains with Valine-Resistant AHAS I

The cassette cat-$P_L$-ilvBN ValR4 was introduced into L-leucine-producing *E. coli* strain 57 (Russian patent RU 2140450, VKPM B-7386). For this purpose, the strain *E. coli* 57 was infected with phage P1$_{vir}$ grown on the donor strain B7 ΔilvIH ΔilvGM cat-$P_L$-ilvBNValR4. The transductants were selected on L-agar plates supplemented with chloramphenicol (20 μg/ml). The strain 57 was deposited in the Russian National Collection of Industrial Microorganisms (VKPM) (Russia, 117545 Moscow, 1 Dorozhny proezd, 1) on May 19, 1997 under accession number VKPM B-7386.

Both *E. coli* strains 57 and 57 cat-$P_L$-ilvBNValR4 were cultivated as shown in Example 6. The accumulated L-leucine was measured by TLC. Results are presented in Table 5.

TABLE 5

| Strain | L-leucine, g/l |
|---|---|
| 57 | 1.6 |
| 57 cat-$P_L$-ilvBN ValR4 | 1.9 |

As shown in Table 5, strain 57 cat-$P_L$-ilvBNValR4 produced a larger amount of L-leucine.

Reference Example 1

Construction of the Plasmid pMIV5JS

Figure 4:
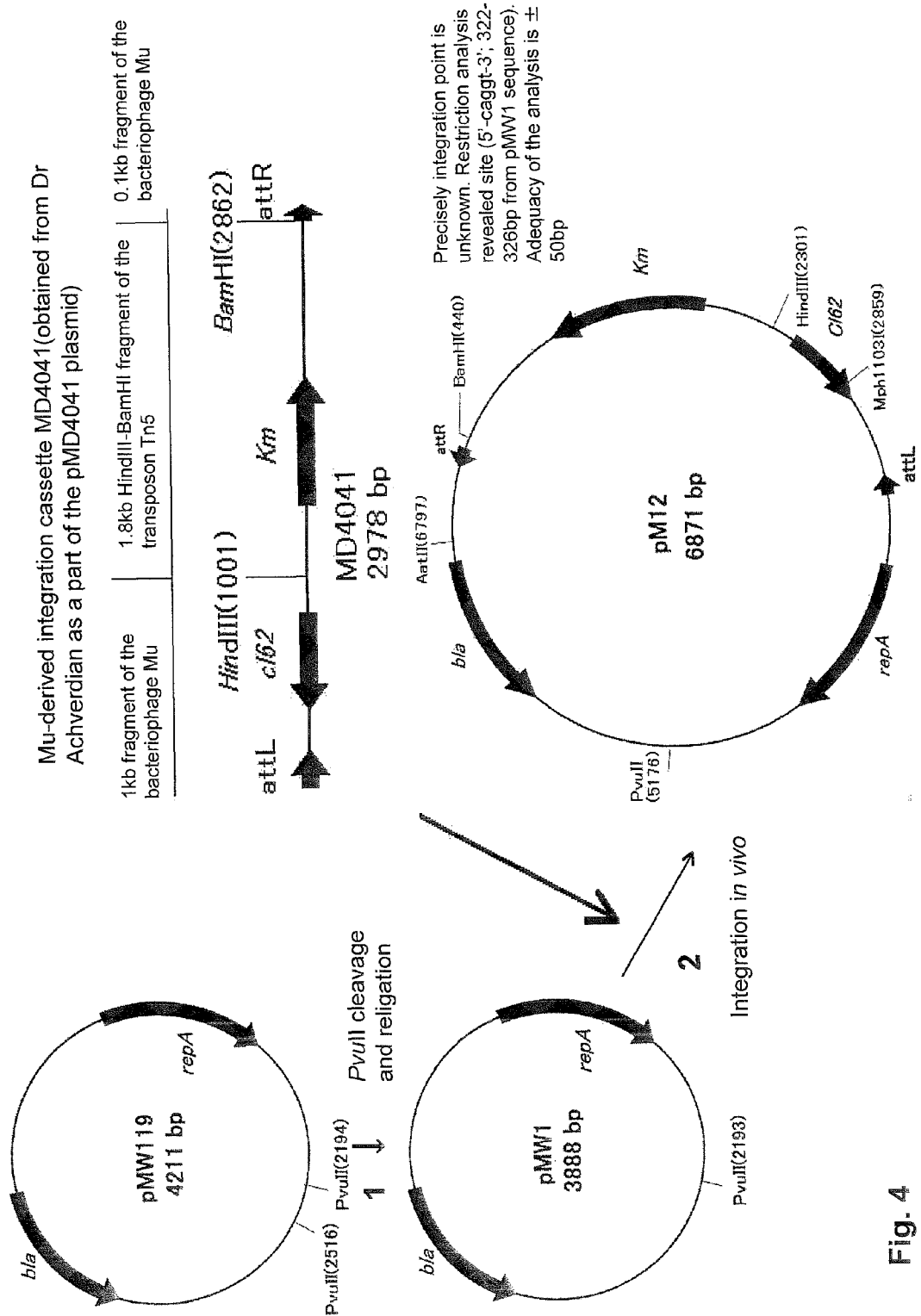
FIG. 4 shows the construction of the plasmid pM12.
Figure 5:
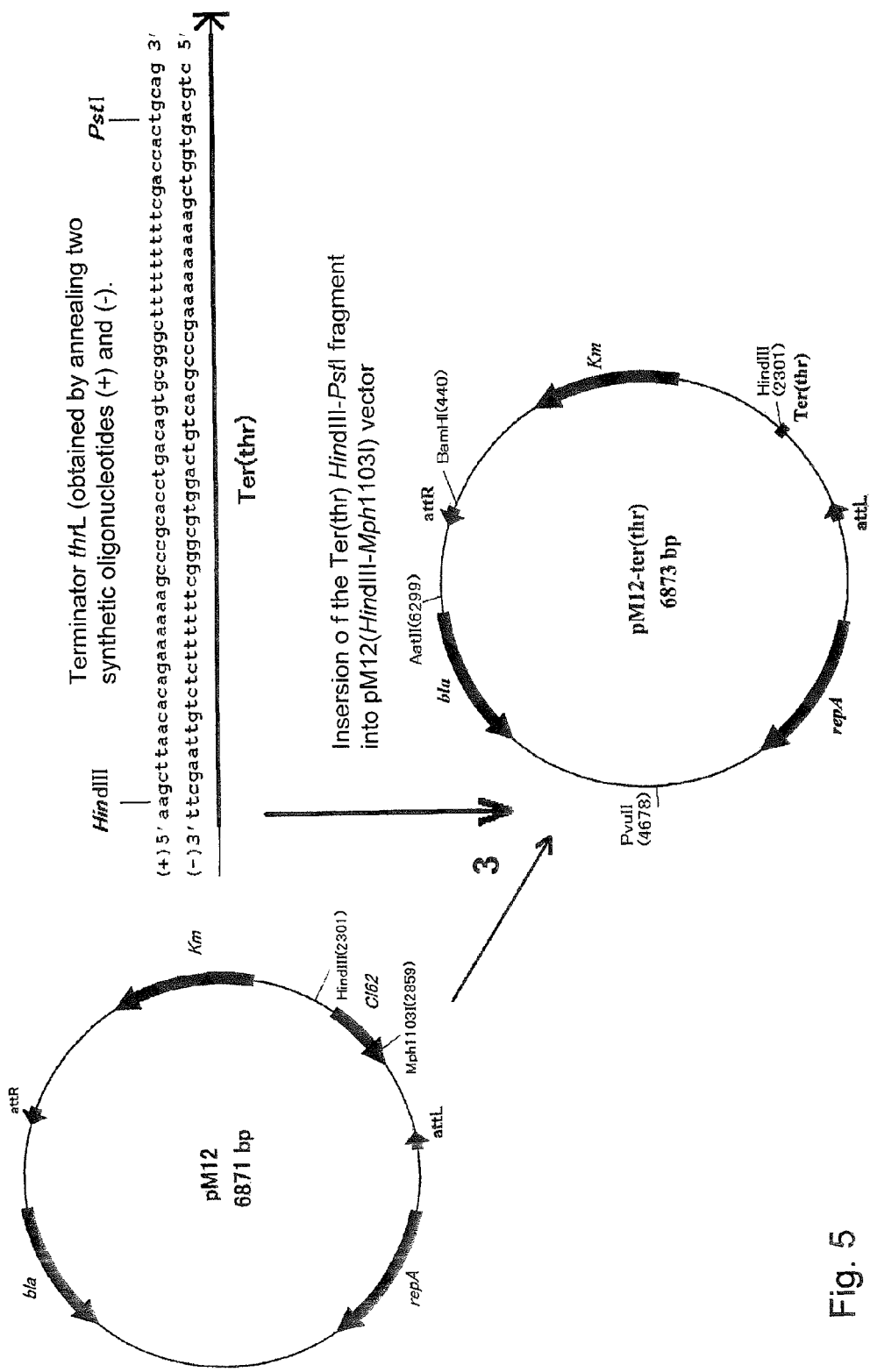
FIG. 5 shows the construction of the plasmid pM12-ter (thr).

PMIV-5JS was constructed according to the following scheme. First, plasmid pM12 was constructed by integrating in vivo a Mu-derived integration cassette into plasmid pMW1, which is a derivative of pMW119 (FIG. 4). Two terminator oligonucleotide sequences complementary to each other were synthesized (SEQ ID NO: 19 and SEQ ID NO: 20). Terminator thrL was obtained by annealing these synthetic oligonucleotides in the forward (SEQ ID NO: 19) and reverse directions (SEQ ID NO: 20). Terminator thrL was flanked with sites HindIII and PstI. Then, plasmid pM12-ter (thr) was constructed by inserting the synthetic terminator sequence Ter(thr) into pM12 which had been digested with HindIII and Mph1103I (FIG. 5).

Figure 6:
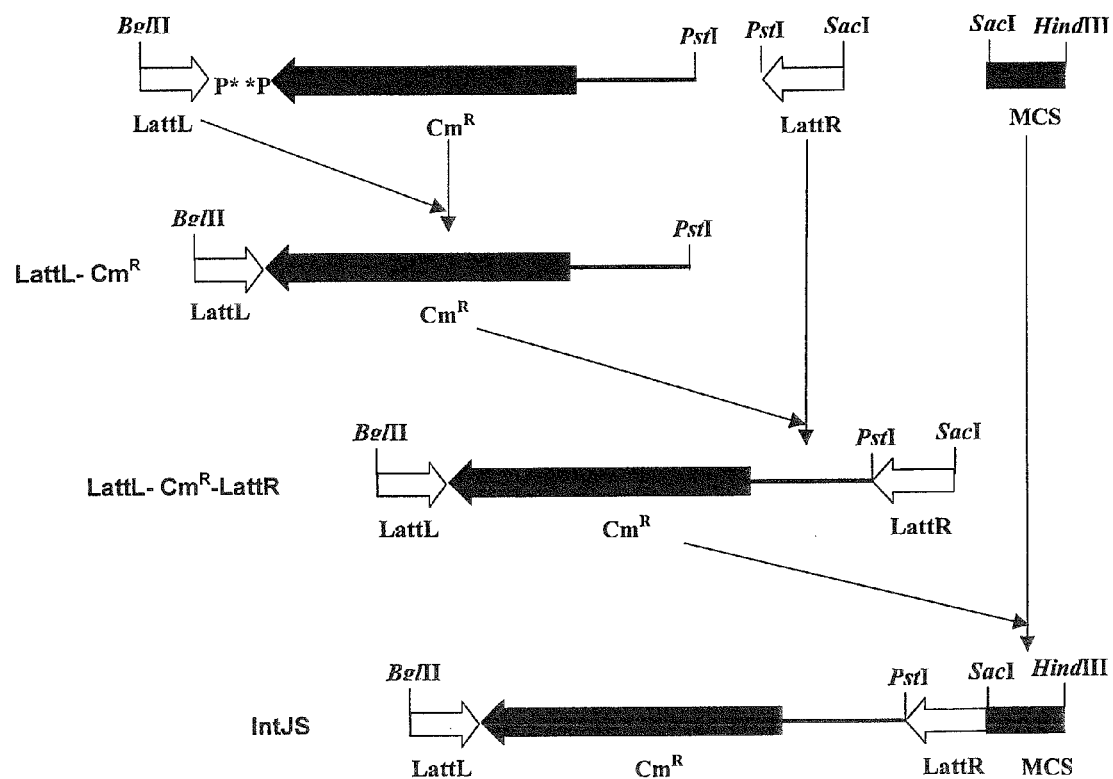
FIG. 6 shows the construction of the intJS integrative cassette.
Figure 7:
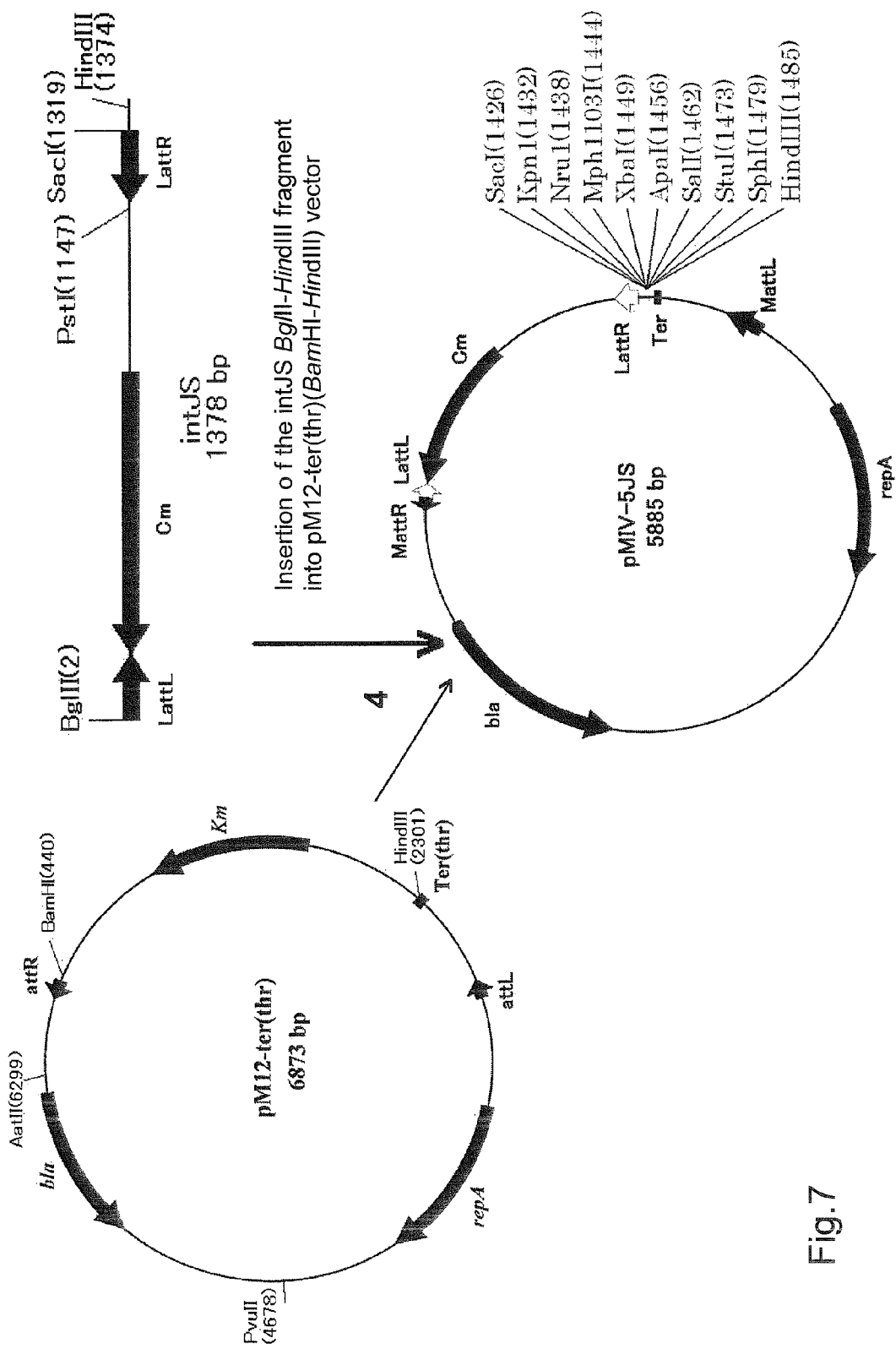
FIG. 7 shows the construction of the plasmid pMIV-5JS.

The intJS integrative cassette was constructed as following (FIG. 6):

a) a 0.12 kbp LattL fragment was obtained by PCR amplification using an upstream primer (SEQ ID NO: 21) (the site for BglII is underlined), and a phosphorylated downstream primer (SEQ ID NO: 22). Plasmid pMW118-attL-tet-attR-ter_rrnB was used as a template (WO2005/010175);

b) a 1.03 kbp Cm$^R$ fragment was obtained by PCR amplification using a phosphorylated upstream primer (SEQ ID NO: 23), and a downstream primer (SEQ ID NO: 24) (the site for PstI is underlined). Plasmid pACYC184 was used as a template;

c) a 0.16 kbp LattR fragment was obtained by PCR amplification using an upstream primer (SEQ ID NO: 25) (the site for PstI is underlined), and a downstream primer (SEQ ID NO: 26) (the site for SacI is underlined). Plasmid pMW118-attL-tet-attR-ter_rrnB was used as a template;

d) fragments LattL and Cm$^R$ were ligated and the resulting 1.15 kbp fragment LattL-Cm$^R$ was purified;

e) fragments LattL-Cm$^R$ and LattR were digested by PstI, ligated, and the resulting 1.31 kbp LattL-Cm$^R$-LattR fragment was purified;

f) a 70 bp double stranded DNA fragment containing multiple cloning sites (MCS) was obtained by annealing two synthesized oligonucleotides: oligonucleotide having sequence depicted in SEQ ID NO: 27 and another oligonucleotide having a sequence complementary to SEQ ID NO: 27;

g) fragments LattL-Cm$^R$-LattR and MCS were digested by SacI, ligated, and the resulting 1.38 kbp cassette LattL-Cm$^R$-LattR-MCS was purified;

For the last step, the fragment LattL-Cm$^R$-LattR-MCS was digested by BglII and HindIII and cloned into pM12-ter(thr) which had been digested with BamHI and HindIII to yield plasmid pMIV-5JS (FIG. 7).

Reference Example 2

Construction of the Strain with Inactivated Acetolactate Synthases Genes

1. Deletion of ilvBN Operon

The ilvBN operon was deleted by the method firstly developed by Datsenko and Wanner (Proc. Natl. Acad. Sci. USA, 2000, 97(12), 6640-6645) called as a "Red-driven integration". According to this procedure, the PCR primers ilvBN1 (SEQ ID NO: 28) and ilvBN2 (SEQ ID NO: 29) homologous to both the region adjacent to the ilvBN operon and the gene conferring chloramphenicol resistance in the template plasmid were constructed. The plasmid pMW-attL-Cm-attR (PCT application WO 05/010175) was used as a template in the PCR reaction. Conditions for PCR were the following: denaturation step for 3 min at 95° C.; profile for two first cycles: 1 min at 95° C., 30 sec at 34° C., 40 sec at 72° C.; profile for the last 30 cycles: 30 sec at 95° C., 30 sec at 50° C., 40 sec at 72° C.; final step: 5 min at 72° C.

The resulting 1713 bp PCR product was purified in agarose gel and used for electroporation of the *E. coli* strain MG1655, which contains the plasmid pKD46 with a temperature-sensitive replication origin. The plasmid pKD46 (Datsenko and Wanner, Proc. Natl. Acad. Sci. USA, 2000, 97:12:6640-45) includes a 2,154 nt (31088-33241) DNA fragment of phage λ (GenBank accession No. J02459), which contains genes of the λ Red homologous recombination system (γ, β, exo genes) under the control of the arabinose-inducible $P_{araB}$ promoter. The plasmid pKD46 is necessary for integration of the PCR product into the chromosome of the *E. coli* strain MG1655.

Electrocompetent cells were prepared as follows: overnight culture of *E. coli* MG1655/pKD46 grown at 30° C. in LB medium, supplemented with ampicillin (100 mg/l), was diluted in 100 times with 5 ml of SOB medium (Sambrook et al, "Molecular Cloning A Laboratory Manual, Second Edition", Cold Spring Harbor Laboratory Press (1989)) with ampicillin and L-arabinose (1 mM). The culture was grown with aeration at 30° C. to an $OD_{600}$ of ≈0.6 and then made electrocompetent by concentrating 100-fold and washing three times with ice-cold deionized $H_2O$. Electroporation was performed using 70 μl of cells and ≈100 ng of PCR product. Cells after electroporation were incubated with 1 ml of SOC medium (Sambrook et al, "Molecular Cloning A Laboratory Manual, Second Edition", Cold Spring Harbor Laboratory Press (1989)) at 37° C. for 2.5 h, plated onto L-agar, and grown at 37° C. to select $Cm^R$ recombinants. Then, to eliminate the pKD46 plasmid, 2 passages on L-agar with Cm at 42° C. were performed and the resulting colonies were tested for sensitivity to ampicillin. Thus, the mutant strain MG1655 ΔilvBN::cat with an inactivated ilvBN operon was constructed.

2. Verification of ilvBN Operon Deletion by PCR.

Figure 8:
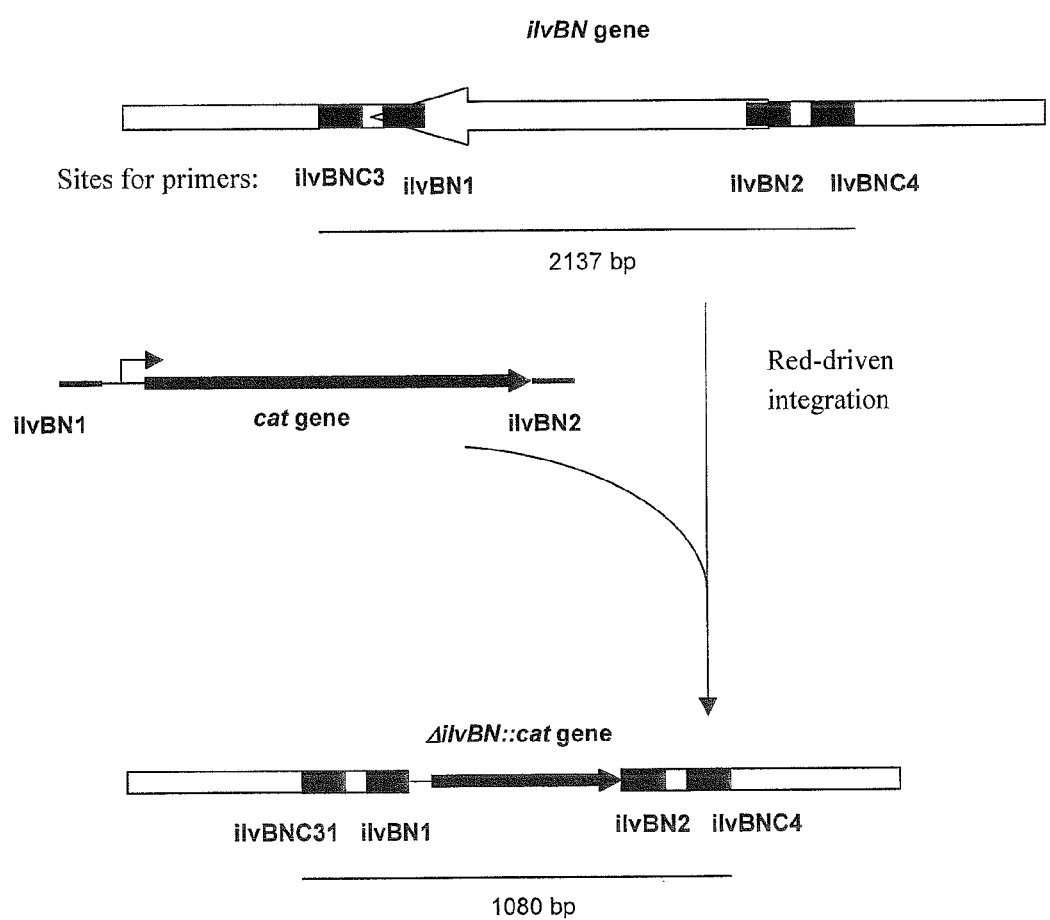
FIG. 8 shows the construction of a chromosomal DNA fragment with the inactivated ilvBN gene.

Mutants with the ilvBN operon deleted and marked with the Cm resistance gene were verified by PCR. Locus-specific primers ilvBNC5 (SEQ ID NO: 30) and ilvBNC6 (SEQ ID NO: 31) were used in PCR for the verification. Conditions for PCR verification were the following: denaturation step for 3 min at 94° C.; profile for the 30 cycles: 30 sec at 94° C., 30 sec at 53° C., 1 min at 72° C.; final step: 7 min at 72° C. The PCR product obtained in the reaction using the chromosomal DNA from parental ilvBN strain MG1655 as a template was 2275 nt in length. The PCR product obtained in the reaction using the chromosomal DNA from mutant MG1655 ΔilvBN::cat strain as a template was 1995 nt in length (FIG. 8).

3. Deletion of ilvIH Operon

The ilvIH operon was deleted by the same methods as the deletion of ilvBN operon described in Section 1. According to this procedure, the PCR primers ilvIH1 (SEQ ID NO: 32) and ilvIH2 (SEQ ID NO: 33) homologous to both the region adjacent to the ilvIH operon and gene conferring chloramphenicol resistance in the template plasmid were constructed. The plasmid pMW-attL-Cm-attR (PCT application WO 05/010175) was used as a template in the PCR reaction. Conditions for PCR were the following: denaturation step for 3 min at 95° C.; profile for two first cycles: 1 min at 95° C., 30 sec at 34° C., 40 sec at 72° C.; profile for the last 30 cycles: 30 sec at 95° C., 30 sec at 50° C., 40 sec at 72° C.; final step: 5 min at 72° C.

The 1713 bp PCR product was purified in an agarose gel and used for electroporation of the *E. coli* strain MG1655/pKD46. Chloramphenicol-resistant recombinants were selected after electroporation and verified by means of PCR with the locus-specific primers ilvIHC3 (SEQ ID NO: 34) and ilvIHC4 (SEQ ID NO: 35). Conditions for PCR verification were the following: denaturation step for 3 min at 94° C.; profile for the 30 cycles: 30 sec at 94° C., 30 sec at 53° C., 1 min 20 sec at 72° C.; final step: 7 min at 72° C. The PCR product obtained in the reaction using the chromosomal DNA from parental IlvIH+ strain MG1655B7 ΔilvBN::cat as a template was 2491 nt in length. The PCR product obtained in the reaction using the chromosomal DNA from mutant MG1655B7 ΔilvBN::cat ΔilvIH::cat strain as a template was 1823 nt in length. As a result, the strain MG1655 ΔilvIH::cat was obtained.

4. Deletion of ilvGM Operon

The ilvGM operon was deleted by the same methods as the deletion of ilvBN operon described in Section 1. According to this procedure, the PCR primers ilvGM1 (SEQ ID NO: 36) and ilvGM2 (SEQ ID NO: 37) homologous to both the region adjacent to the ilvGM operon and the gene conferring chloramphenicol-resistance in the template plasmid were constructed. The plasmid pMW-attL-Cm-attR (PCT application WO 05/010175) was used as a template in the PCR reaction. Conditions for PCR were the following: denaturation step for 3 min at 95° C.; profile for two first cycles: 1 min at 95° C., 30 sec at 34° C., 40 sec at 72° C.; profile for the last 30 cycles: 30 sec at 95° C., 30 sec at 50° C., 40 sec at 72° C.; final step: 5 min at 72° C.

The 1713 bp PCR product was purified in an agarose gel and used for electroporation of the *E. coli* strain MG1655/pKD46. Chloramphenicol-resistant recombinants were selected after electroporation and verified by PCR with the locus-specific primers ilvGMC3 (SEQ ID NO: 38) and ilvGMC4 (SEQ ID NO: 39). Conditions for PCR verification were the following: denaturation step for 3 min at 94° C.; profile for the 30 cycles: 30 sec at 94° C., 30 sec at 54° C., 1 min 30 sec at 72° C.; final step: 7 min at 72° C. The PCR product obtained in the reaction using the chromosomal DNA from parental strain MG1655 as a template was 2209 nt in length. The PCR product obtained in the reaction using the chromosomal DNA from mutant MG1655 ΔilvGM::cat strain as a template was 1941 nt in length. As a result, the strain MG1655 ΔilvGM::cat was obtained.

5. Construction of Strains with all the Acetolactate Synthase Genes Inactivated (Combination of ΔilvBN, ΔilvIH and ΔilvGM Deletions).

The ilvIH genes (ΔilvIH::cat) were deleted in the wild-type strain *E. coli* K12 (VKPM B-7) by P1 transduction (Sambrook et al, "Molecular Cloning A Laboratory Manual, Second Edition", Cold Spring Harbor Laboratory Press (1989). The *E. coli* strain MG1655 ΔilvIH::cat described in Section 3 was used as a donor strain, and CmR transductants were selected. As a result, the strain B7 ΔilvIH::cat was obtained. To eliminate the chloramphenicol resistance marker from B7 ΔilvIH::cat, cells were transformed with the plasmid pMW118-int-xis (Ap$^R$) (WO2005/010175). Ap$^R$ clones were grown on LB agar plates containing 150 mg/l ampicillin at 30° C. Several tens of Ap$^R$ clones were picked up and tested for chloramphenicol sensitivity. The plasmid pMW118-int-xis was eliminated from the Cm$^S$ cells by incubation on LB agar plates at 42° C. As a result, the strain B7 ΔilvIH was obtained.

The ilvBN genes (ΔilvBN::cat) were deleted in the *E. coli* strain B7 ΔilvIH by P1 transduction. The strain *E. coli* MG1655 ΔilvBN::cat described in Section 1 was used as a donor strain, and CmR transductants were selected. As a result, the strain B7 ΔilvIH ΔilvBN::cat was obtained. The chloramphenicol resistance marker was eliminated from B7 ΔilvIH ΔilvBN::cat as described above. As a result, the strain B7 ΔilvIH ΔilvBN was obtained.

The ilvGM genes (ΔilvGM::cat) were deleted in the *E. coli* strains B7 ΔilvIH by P1 transduction. The strain *E. coli* MG1655 ΔilvGM::cat described in Section 4 was used as a donor strain, and CmR transductants were selected. As a result, the strain B7 ΔilvIH ΔilvGM::cat was obtained. The chloramphenicol resistance marker was eliminated from B7 ΔilvIH ΔilvGM::cat as described above. As a result, the strain B7 ΔilvIH ΔilvGM was obtained. The strain B7 ΔilvIH ΔilvGM was prototrophic, therefore deletion of ilvGM genes did not prevent expression of the distal genes of the isoleucine-valine operon.

The ilvGM genes (ΔilvGM::cat) were deleted in the *E. coli* strains B7 ΔilvIH ΔilvBN by P1 transduction. The strain *E. coli* MG1655 ΔilvGM::cat described in Section 4 was used as a donor strain; CmR transductants were selected. As a result, the strain B7 ΔilvIH ΔilvBN ΔilvGM::cat was obtained. The chloramphenicol resistance marker was eliminated from B7 ΔilvIH ΔilvBN ΔilvGM::cat as described above. As a result, the strain B7 ΔilvIH ΔilvBN ΔilvGM was obtained.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

What is claimed is:

1. A method for producing a branched-chain L-amino acid comprising cultivating a recombinant microorganism from the Enterobacteriaceae family in a culture medium, and collecting the branched-chain L-amino acids from the culture medium, wherein said recombinant microorganism has been transformed with a vector comprising an isolated DNA coding for a mutant small subunit of bacterial acetolactate synthase (AHAS I) or the isolated DNA has been introduced into the chromosome of said recombinant microorganism, wherein the amino acid sequence of said mutant small subunit comprises the amino acid sequence shown in SEQ ID NO: 2, and also comprises a mutation selected from the group consisting of:

A) replacing the L-amino acid at position 17 in the amino acid sequence of SEQ ID NO: 2 with a lysine residue, B) replacing the L-amino acid at position 30 in the amino acid sequence of SEQ ID NO: 2 with another L-amino acid, C) replacing the sequence from the L-amino acid at position 44 to the C-terminus in the amino acid sequence of SEQ ID NO: 2 with 1 to 10 L-amino acids, and D) combinations thereof; and wherein said bacterial acetolactate synthase comprising said mutant small subunit is expressed, and is desensitized to feedback inhibition by valine.

2. The method according to claim 1, wherein the amino acid sequence of said mutant small subunit comprises the mutations A), B), and C).

3. The method according to claim 1, wherein said branched-chain L-amino acids are selected from the group consisting of L-leucine, L-isoleucine, and L-valine.

4. The method according to claim 1, wherein the activity of the bacterial acetolactate synthase in the recombinant microorganism is enhanced as compared to a wild-type strain of the microorganism.

5. The method according to claim 1, wherein the recombinant microorganism belongs to the genus *Escherichia*.

6. The method according to claim 4, wherein the activity of the bacterial acetolactate synthase is enhanced by increasing the expression of said DNA coding for a mutant small subunit of bacterial acetolactate synthase.

7. The method according to claim 6, wherein the activity of the bacterial acetolactate synthase is increased by a method selected from the group consisting of:

a) increasing the copy number of said DNA coding for a mutant small subunit of bacterial acetolactate synthase, b) modifying an expression control sequence of said DNA coding for a mutant small subunit of bacterial acetolactate synthase so that the expression of said DNA is enhanced, and c) combinations thereof.

8. The method according to claim 7, wherein the copy number is increased by the integration of multiple copies of said DNA coding for a mutant small subunit of bacterial acetolactate synthase into the chromosome of the bacterium.

9. The method according to claim 1, wherein said L-amino acid at position 30 is replaced with a proline residue.

10. The method according to claim 5, wherein the recombinant microorganism belongs to *Escherichia coli*.

* * * * *

SEQUENCE LISTING

```
<160> NUMBER OF SEQ ID NOS: 39

<210> SEQ ID NO 1
<211> LENGTH: 291
<212> TYPE: DNA
<213> ORGANISM: Escherichia coli
<220> FEATURE:
<221> NAME/KEY: CDS
<222> LOCATION: (1)..(291)

<400> SEQUENCE: 1 atg caa aac aca act cat gac aac gta att ctg gag ctc acc gtt cgc        48
Met Gln Asn Thr Thr His Asp Asn Val Ile Leu Glu Leu Thr Val Arg
1               5                   10                  15 aac cat ccg ggc gta atg acc cac gtt tgt ggc ctt ttt gcc cgc cgc        96
Asn His Pro Gly Val Met Thr His Val Cys Gly Leu Phe Ala Arg Arg
            20                  25                  30 gct ttt aac gtt gaa ggc att ctt tgt ctg ccg att cag gac agc gac       144
Ala Phe Asn Val Glu Gly Ile Leu Cys Leu Pro Ile Gln Asp Ser Asp
        35                  40                  45 aaa agc cat atc tgg cta ctg gtc aat gac gac cag cgt ctg gag cag       192
Lys Ser His Ile Trp Leu Leu Val Asn Asp Asp Gln Arg Leu Glu Gln
    50                  55                  60 atg ata agc caa atc gat aag ctg gaa gat gtc gtg aaa gtg cag cgt       240
Met Ile Ser Gln Ile Asp Lys Leu Glu Asp Val Val Lys Val Gln Arg
65                  70                  75                  80 aat cag tcc gat ccg acg atg ttt aac aag atc gcg gtg ttt ttt cag       288
Asn Gln Ser Asp Pro Thr Met Phe Asn Lys Ile Ala Val Phe Phe Gln
                85                  90                  95 taa                                                                    291

<210> SEQ ID NO 2
<211> LENGTH: 96
<212> TYPE: PRT
<213> ORGANISM: Escherichia coli

<400> SEQUENCE: 2

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
```

```
            20                  25                  30
Ala Phe Asn Val Glu Gly Ile Leu Cys Leu Pro Ile Gln Asp Ser Asp
            35                  40                  45

Lys Ser His Ile Trp Leu Leu Val Asn Asp Asp Gln Arg Leu Glu Gln
        50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95
```

<210> SEQ ID NO 3
<211> LENGTH: 27
<212> TYPE: DNA
<213> ORGANISM: Artificial
<220> FEATURE:
<223> OTHER INFORMATION: primer ilvBX60

<400> SEQUENCE: 3
actctagacg actgacgaaa cctcgct                                        27

<210> SEQ ID NO 4
<211> LENGTH: 29
<212> TYPE: DNA
<213> ORGANISM: Artificial
<220> FEATURE:
<223> OTHER INFORMATION: primer ilvBR64

<400> SEQUENCE: 4
aggtcgacgt gatcatggtc ttgtcctgg                                      29

<210> SEQ ID NO 5
<211> LENGTH: 26
<212> TYPE: DNA
<213> ORGANISM: Artificial
<220> FEATURE:
<223> OTHER INFORMATION: primer ML74

<400> SEQUENCE: 5
cctgttcatg aatcccatac tttgac                                         26

<210> SEQ ID NO 6
<211> LENGTH: 26
<212> TYPE: DNA
<213> ORGANISM: Artificial
<220> FEATURE:
<223> OTHER INFORMATION: primer LattRS1

<400> SEQUENCE: 6
ccatctaagt agttgattca tagtga                                         26

<210> SEQ ID NO 7
<211> LENGTH: 21
<212> TYPE: DNA
<213> ORGANISM: Artificial
<220> FEATURE:
<223> OTHER INFORMATION: primer ilvbS31

<400> SEQUENCE: 7
caacatcgac gcgtaagcgc t                                              21

<210> SEQ ID NO 8
<211> LENGTH: 23
<212> TYPE: DNA
<213> ORGANISM: Artificial

```
<220> FEATURE:
<223> OTHER INFORMATION: primer ilvbS32

<400> SEQUENCE: 8
gcgaagaaag cattcgtgac gca                                           23

<210> SEQ ID NO 9
<211> LENGTH: 23
<212> TYPE: DNA
<213> ORGANISM: Artificial
<220> FEATURE:
<223> OTHER INFORMATION: primer ilvbS33

<400> SEQUENCE: 9
cgcctgtgtc gatgacaatg caa                                           23

<210> SEQ ID NO 10
<211> LENGTH: 1830
<212> TYPE: DNA
<213> ORGANISM: Artificial
<220> FEATURE:
<223> OTHER INFORMATION: mutant ilvBN gene

<400> SEQUENCE: 10
atggcaagtt cgggcacaac atcgacgcgt aagcgcttta ccggcgcaga atttatcgtt     60
catttcctgg aacagcaggg cattaagatt gtgacaggca ttccgggcgg ttctatcctg    120
cctgtttacg atgccttaag ccaaagcacg caaatccgcc atattctggc ccgtcatgaa    180
cagggcgcgg gctttatcgc tcagggaatg gcgcgcaccg acgtaaaacc ggcggtctgt    240
atggcctgta gcggaccggg tgcgactaac ctggtgaccg ccattgccga tgcgcggctg    300
gactccatcc cgctgatttg catcactggt caggttcccg cctcgatgat cggcaccgac    360
gccttccagg aagtggacac ctacggcatc tctatcccca tcaccaaaca caactatctg    420
gtcagacata tcgaagaact cccgcaggtc atgagcgatg ccttccgcat tgcgcaatca    480
ggccgcccag gcccggtgtg gatagacatt cctaaggatg tgcaaacggc agttttttgag    540 attgaaacac agcccgctat ggcagaaaaa gccgccgccc ccgcctttag cgaagaaagc    600
attcgtgacg cagcggcgat gattaacgct gccaaacgcc cggtgcttta tctgggcggc    660
ggtgtgatca atgcgcccgc acgggtgcgt gaactggcgg agaaagcgca actgcctacc    720
accatgactt taatggcgct gggcatgttg ccaaaagcgc atccgttgtc gctgggtatg    780
ctggggatgc acggcgtgcg cagcaccaac tatattttgc aggaggcgga tttgttgata    840
gtgctcggtg cgcgttttga tgaccgggcg attggcaaaa ccgagcagtt ctgtccgaat    900
gccaaaatca ttcatgtcga tatcgaccgt gcagagctgg gtaaaatcaa gcagccgcac    960
gtggcgattc aggcggatgt tgatgacgtg ctggcgcagt gatcccgct ggtggaagcg    1020 caaccgcgtg cagagtggca ccagttggta gcggatttgc agcgtgagtt ccgtgtcca    1080 atcccgaaag cgtgcgatcc gttaagccat tacggcctga tcaacgccgt tgccgcctgt   1140
gtcgatgaca atgcaattat caccaccgac gttggtcagc atcagatgtg gaccgcgcaa   1200
gcttatccgc tcaatcgccc acgccagtgg ctgacctccg gtgggctggg cacgatgggt   1260
tttggcctgc ctgcggcgat tggcgctgcg ctggcgaacc cggatcgcaa agtgttgtgt   1320
ttctccggcg acggcagcct gatgatgaat attcaggaga tggcgaccgc cagtgaaaat   1380
cagctggatg tcaaaatcat tctgatgaac aacgaagcgc tggggctggt gcatcagcaa   1440
cagagtctgt tctacgagca aggcgttttt gccgccacct atccgggcaa aatcaacttt   1500
```

```
atgcagattg ccgccggatt cggcctcgaa acctgtgatt tgaataacga agccgatccg    1560
caggcttcat tgcaggaaat catcaatcgc cctggcccgg cgctgatcca tgtgcgcatt    1620
gatgccgaag aaaaagttta cccgatggtg ccgccaggtg cggcgaatac tgaaatggtg    1680
ggggaataag ccatgcaaaa cacaactcat gacaacgtaa ttctggagct caccgttcgc    1740
aaccatccgg gcgtaatgac ccacgtttgt ggccttttg cccgccgcgc ttttaacgtt    1800
gaaggcattc tttgtctgcc gcgcttttaa                                    1830
```

```
<210> SEQ ID NO 11
<211> LENGTH: 45
<212> TYPE: PRT
<213> ORGANISM: Artificial
<220> FEATURE:
<223> OTHER INFORMATION: Synthesized

<400> SEQUENCE: 11

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
            20                  25                  30

Ala Phe Asn Val Glu Gly Ile Leu Cys Leu Pro Arg Phe
        35                  40                  45

<210> SEQ ID NO 12
<211> LENGTH: 64
<212> TYPE: DNA
<213> ORGANISM: Artificial
<220> FEATURE:
<223> OTHER INFORMATION: primer ilvB-attR1

<400> SEQUENCE: 12
ccgcaggcga ctgacgaaac ctcgctccgg cggggtcgct caagttagta taaaaaagct    60
gaac                                                                64

<210> SEQ ID NO 13
<211> LENGTH: 64
<212> TYPE: DNA
<213> ORGANISM: Artificial
<220> FEATURE:
<223> OTHER INFORMATION: primer ilvB-PLSD

<400> SEQUENCE: 13
tgcccgaact tgccatgctc cagtctcctt cttctgagct gtttccttct agacggccaa    60
tgct                                                                64

<210> SEQ ID NO 14
<211> LENGTH: 1968
<212> TYPE: DNA
<213> ORGANISM: Artificial
<220> FEATURE:
<223> OTHER INFORMATION: DNA fragment containing cat gene and PL
      promoter

<400> SEQUENCE: 14
ccgcaggcga ctgacgaaac ctcgctccgg cggggtcgct caagttagta taaaaaagct    60
gaacgagaaa cgtaaaatga tataaatatc aatatattaa attagatttt gcataaaaaa    120
cagactacat aatactgtaa aacacaacat atgcagtcac tatgaatcaa ctacttagat    180
ggtattagtg acctgtaaca gactgcagtg gtcgaaaaaa aaagcccgca ctgtcaggtg    240
cgggcttttt tctgtgttaa gcttcgacga atttctgcca ttcatccgct tattatcact    300
```

```
tattcaggcg tagcaccagg cgtttaaggg caccaataac tgccttaaaa aaattacgcc    360
ccgccctgcc actcatcgca gtactgttgt aattcattaa gcattctgcc gacatggaag    420
ccatcacaga cggcatgatg aacctgaatc gccagcggca tcagcacctt gtcgccttgc    480
gtataatatt tgcccatggt gaaaacgggg gcgaagaagt tgtccatatt ggccacgttt    540
aaatcaaaac tggtgaaact cacccaggga ttggctgaga cgaaaaacat attctcaata    600 aacccctttag ggaaataggc caggttttca ccgtaacacg ccacatcttg cgaatatatg    660
tgtagaaact gccggaaatc gtcgtggtat tcactccaga gcgatgaaaa cgtttcagtt    720
tgctcatgga aaacggtgta acaagggtga acactatccc atatcaccag ctcaccgtct    780
ttcattgcca tacggaattc cggatgagca ttcatcaggc gggcaagaat gtgaataaag    840
gccggataaa acttgtgctt atttttcttt acggtcttta aaaaggccgt aatatccagc    900
tgaacggtct ggttataggt acattgagca actgactgaa atgcctcaaa atgttcttta    960
cgatgccatt gggatatatc aacggtggta tatccagtga tttttttctc cattttagct    1020
tccttagctc ctgaaaatct cggatccgat atctagctag agcgcccggt tgacgctgct    1080
agtgttacct agcgatttgt atcttactgc atgttacttc atgttgtcaa tacctgtttt    1140
tcgtgcgact tatcaggctg tctacttatc cggagatcca caggacgggt gtggtcgcca    1200
tgatcgcgta gtcgatagtg gctccaagta gcgaagcgag caggactggg cggcggccaa    1260
agcggtcgga cagtgctccg agaacgggtg cgcatagaaa ttgcatcaac gcatatagcg    1320
ctagcagcac gccatagtga ctggcgatgc tgtcggaatg gacgatatcc cgcaagaggc    1380
ccggcagtac cggcataacc aagcctatgc ctacagcatc cagggtgacg gtgccgagga    1440
tgacgatgag cgcattgtta gatttcatac acggtgcctg actgcgttag caatttaact    1500
gtgataaact accgcattaa agcttatcga tgataagctg tcaaacatga gaattcgaaa    1560
tcaaataatg attttatttt gactgatagt gacctgttcg ttgcaacaaa ttgataagca    1620
atgctttttt ataatgccaa cttagtataa aaaagcaggc ttcaagatct tcacctacca    1680
aacaatgccc ccctgcaaaa aataaattca tataaaaaac atacagataa ccatctgcgg    1740
tgataaatta tctctggcgg tgttgacata ataccactg gcggtgatac tgagcacatc     1800
agcaggacgc actgaccacc atgaaggtga cgctcttaaa aattaagccc tgaagaaggg    1860
cagcattcaa agcagaaggc tttggggtgt gtgatacgag acgaagcatt ggccgtctag    1920
aaggaaacag ctcagaagaa ggagactgga gcatggcaag ttcgggca                 1968
```

<210> SEQ ID NO 15
<211> LENGTH: 23
<212> TYPE: DNA
<213> ORGANISM: Artificial
<220> FEATURE:
<223> OTHER INFORMATION: primer MR74

<400> SEQUENCE: 15
tgaagcggcg cacgaaaaac gcg                                              23

<210> SEQ ID NO 16
<211> LENGTH: 21
<212> TYPE: DNA
<213> ORGANISM: Artificial
<220> FEATURE:
<223> OTHER INFORMATION: primer Cm-test2

<400> SEQUENCE: 16
ttcatcgctc tggagtgaat a                                            21

<210> SEQ ID NO 17
<211> LENGTH: 586
<212> TYPE: DNA
<213> ORGANISM: Artificial
<220> FEATURE:
<223> OTHER INFORMATION: native ilvBN regulator region

<400> SEQUENCE: 17
tgaagcggcg cacgaaaaac gcgaaagcgt tcacgataaa atgcgaaaac tttagctttc    60
gcgcttcaaa tgaaacagat gtattaatta ctgcttttta ttcattacat ggggatcttg   120
aagcctgctt ttttatacta agttggcatt ataaaaagca ttgcttatca atttgttgca   180
acgaacaggt cactatcagt caaaataaaa tcattatttg atttcgtcga gttacgcccc   240
gccctgccac tcatcgcagt actgttgtaa ttcattaagc attctgccga catggaagcc   300
atcacagacg gcatgatgaa cctgaatcgc cagcggcatc agcaccttgt cgccttgcgt   360
ataatatttg cccatggtga aaacgggggc gaagaagttg tccatattgg ccacgtttaa   420
atcaaaactg gtgaaactca cccagggatt ggctgagacg aaaaacatat tctcaataaa   480
cccctttaggg aaataggcca ggttttcacc gtaaacgcc acatcttgcg aatatatgtg    540
tagaaactgc cggaaatcgt cgtggtattc actccagagc gatgaa                 586

<210> SEQ ID NO 18
<211> LENGTH: 879
<212> TYPE: DNA
<213> ORGANISM: Artificial
<220> FEATURE:
<223> OTHER INFORMATION: ilvBN regulator region after modification

<400> SEQUENCE: 18
tgaagcggcg cacgaaaaac gcgaaagcgt tcacgataaa atgcgaaaac tttagctttc    60
gcgcttcaaa tgaaacagat gtattaatta ctgcttttta ttcattacat ggggatcttg   120
aagcctgctt ttttatacta acttgagcgg agctcggtac ctcgcgaatg catctagacg   180
actgacgaaa cctcgctccg gcggggtcgc tcaagttagt ataaaaaagc tgaacgagaa   240
acgtaaaatg atataaatat caatatatta aattagattt tgcataaaaa acagactaca   300
taatactgta aaacacaaca tatgcagtca ctatgaatca actacttaga tggtattagt   360
gacctgtaac agactgcagt ggtcgaaaaa aaaagcccgc actgtcaggt gcgggctttt   420
ttctgtgtta agcttcgacg aatttctgcc attcatccgc ttattatcac ttattcaggc   480
gtagcaccag gcgtttaagg gcaccaataa ctgccttaaa aaaattacgc cccgccctgc   540
cactcatcgc agtactgttg taattcatta agcattctgc cgacatggaa gccatcacag   600
acggcatgat gaacctgaat cgccagcggc atcagcacct tgtcgccttg cgtataatat   660
ttgcccatgg tgaaacggg ggcgaagaag ttgtccatat tggccacgtt taaatcaaaa   720
ctggtgaaac tcacccaggg attggctgag acgaaaaaca tattctcaat aaacccttta   780
gggaaatagg ccaggttttc accgtaacac gccacatctt gcgaatatat gtgtagaaac   840
tgccggaaat cgtcgtggta ttcactccag agcgatgaa                         879

<210> SEQ ID NO 19
<211> LENGTH: 62
<212> TYPE: DNA
<213> ORGANISM: Artificial
<220> FEATURE:
<223> OTHER INFORMATION: forward terminator synthetic oligonucleotide

<400> SEQUENCE: 19
aagcttaaca cagaaaaaag cccgcacctg acagtgcggg cttttttttt cgaccactgc    60
ag                                                                   62

<210> SEQ ID NO 20
<211> LENGTH: 62
<212> TYPE: DNA
<213> ORGANISM: Artificial
<220> FEATURE:
<223> OTHER INFORMATION: reveres terminator synthetic oligonucleotide

<400> SEQUENCE: 20
ttcgaattgt gtctttttc gggcgtggac tgtcacgccc gaaaaaaaaa gctggtgacg     60
tc                                                                   62

<210> SEQ ID NO 21
<211> LENGTH: 37
<212> TYPE: DNA
<213> ORGANISM: Artificial
<220> FEATURE:
<223> OTHER INFORMATION: primer

<400> SEQUENCE: 21
ccagatcttg aagcctgctt ttttatacta agttggc                             37

<210> SEQ ID NO 22
<211> LENGTH: 25
<212> TYPE: DNA
<213> ORGANISM: Artificial
<220> FEATURE:
<223> OTHER INFORMATION: primer

<400> SEQUENCE: 22
gaaatcaaat aatgatttta ttttg                                          25

<210> SEQ ID NO 23
<211> LENGTH: 26
<212> TYPE: DNA
<213> ORGANISM: Artificial
<220> FEATURE:
<223> OTHER INFORMATION: primer

<400> SEQUENCE: 23
ttacgccccg ccctgccact catcgc                                         26

<210> SEQ ID NO 24
<211> LENGTH: 34
<212> TYPE: DNA
<213> ORGANISM: Artificial
<220> FEATURE:
<223> OTHER INFORMATION: primer

<400> SEQUENCE: 24
gtcactgcag ctgatgtccg gcggtgcttt tgcc                                34

<210> SEQ ID NO 25
<211> LENGTH: 31
<212> TYPE: DNA
<213> ORGANISM: Artificial
<220> FEATURE:
<223> OTHER INFORMATION: primer

<400> SEQUENCE: 25

```
cagctgcagt ctgttacagg tcactaatac c                                    31
```

<210> SEQ ID NO 26
<211> LENGTH: 37
<212> TYPE: DNA
<213> ORGANISM: Artificial
<220> FEATURE:
<223> OTHER INFORMATION: primer

<400> SEQUENCE: 26

```
ccgagctccg ctcaagttag tataaaaaag ctgaacg                              37
```

<210> SEQ ID NO 27
<211> LENGTH: 70
<212> TYPE: DNA
<213> ORGANISM: Artificial
<220> FEATURE:
<223> OTHER INFORMATION: primer

<400> SEQUENCE: 27

```
cccgagctcg gtacctcgcg aatgcatcta gatgggcccg tcgactgcag aggcctgcat     60
gcaagcttcc                                                            70
```

<210> SEQ ID NO 28
<211> LENGTH: 64
<212> TYPE: DNA
<213> ORGANISM: Artificial
<220> FEATURE:
<223> OTHER INFORMATION: primer ilvBN1

<400> SEQUENCE: 28

```
taaacatcgt cggatcggac tgattacgct gcactttgaa gcctgctttt ttatactaag     60
ttgg                                                                  64
```

<210> SEQ ID NO 29
<211> LENGTH: 64
<212> TYPE: DNA
<213> ORGANISM: Artificial
<220> FEATURE:
<223> OTHER INFORMATION: primer ilvBN2

<400> SEQUENCE: 29

```
tcccggaaag tcggcccaga agaaaaggac tggagccgct caagttagta taaaaaagct     60
gaac                                                                  64
```

<210> SEQ ID NO 30
<211> LENGTH: 24
<212> TYPE: DNA
<213> ORGANISM: Artificial
<220> FEATURE:
<223> OTHER INFORMATION: primer ilvBNC5

<400> SEQUENCE: 30

```
gtctataagg gcaacggtga tcat                                            24
```

<210> SEQ ID NO 31
<211> LENGTH: 24
<212> TYPE: DNA
<213> ORGANISM: Artificial
<220> FEATURE:
<223> OTHER INFORMATION: primer ilvBNC6

<400> SEQUENCE: 31

```
catgctcaac gcaaaactac tacc                                            24
```

<210> SEQ ID NO 32
<211> LENGTH: 61
<212> TYPE: DNA
<213> ORGANISM: Artificial
<220> FEATURE:
<223> OTHER INFORMATION: primer ilvIH1

<400> SEQUENCE: 32
ttcacctttc ctcctgttta ttcttattac ccctgaagcc tgcttttta tactaagttg    60
g                                                                  61

<210> SEQ ID NO 33
<211> LENGTH: 64
<212> TYPE: DNA
<213> ORGANISM: Artificial
<220> FEATURE:
<223> OTHER INFORMATION: primer ilvIH2

<400> SEQUENCE: 33
acatgttggg ctgtaaattg cgcattgaga tcattccgct caagttagta taaaaagct    60
gaac                                                               64

<210> SEQ ID NO 34
<211> LENGTH: 21
<212> TYPE: DNA
<213> ORGANISM: Artificial
<220> FEATURE:
<223> OTHER INFORMATION: primer ilvIHC3

<400> SEQUENCE: 34
ttgctgtaag ttgtgggatt c                                            21

<210> SEQ ID NO 35
<211> LENGTH: 20
<212> TYPE: DNA
<213> ORGANISM: Artificial
<220> FEATURE:
<223> OTHER INFORMATION: primer ilvIHC4

<400> SEQUENCE: 35
tccaggttcc cactgatttc                                              20

<210> SEQ ID NO 36
<211> LENGTH: 64
<212> TYPE: DNA
<213> ORGANISM: Artificial
<220> FEATURE:
<223> OTHER INFORMATION: primer ilvGM1

<400> SEQUENCE: 36
gtttctcaag attcaggacg gggaactaac tatgaatgaa gcctgctttt ttatactaag   60
ttgg                                                               64

<210> SEQ ID NO 37
<211> LENGTH: 64
<212> TYPE: DNA
<213> ORGANISM: Artificial
<220> FEATURE:
<223> OTHER INFORMATION: primer ilvGM2

<400> SEQUENCE: 37
tcagctttct tcgtggtcat ttttatattc cttttgcgct caagttagta taaaaaagct   60

```
gaac                                                                64

<210> SEQ ID NO 38
<211> LENGTH: 20
<212> TYPE: DNA
<213> ORGANISM: Artificial
<220> FEATURE:
<223> OTHER INFORMATION: primer ilvGMC3

<400> SEQUENCE: 38
tggtcgtgat tagcgtggtg                                               20

<210> SEQ ID NO 39
<211> LENGTH: 20
<212> TYPE: DNA
<213> ORGANISM: Artificial
<220> FEATURE:
<223> OTHER INFORMATION: primer ilvGMC4

<400> SEQUENCE: 39
cacatgcacc ttcgcgtctt                                               20
```